US012583835B2

(12) United States Patent
Wu et al.

(10) Patent No.: US 12,583,835 B2
(45) Date of Patent: *Mar. 24, 2026

(54) CRYSTAL FORM OF NITROXOLINE PRODRUG, PHARMACEUTICAL COMPOSITION CONTAINING SAME, AND PREPARATION METHOD THEREFOR AND APPLICATION THEREOF

(71) Applicants: Jiangsu Yahong Meditech Co., Ltd., Taizhou (CN); Asieris Pharmaceuticals (Shanghai) Co., Ltd., Shanghai (CN)

(72) Inventors: Liang Wu, Taizhou (CN); Chen Zhou, Taizhou (CN); Yijun Deng, Taizhou (CN)

(73) Assignees: Jiangsu Yahong Meditech Co., Ltd., Taizhou Jiangsu (CN); Asieris Pharmaceuticals (Shanghai) Co., Ltd., Shanghai (CN)

(*) Notice: Subject to any disclaimer, the term of this patent is extended or adjusted under 35 U.S.C. 154(b) by 701 days.

This patent is subject to a terminal disclaimer.

(21) Appl. No.: 17/906,996

(22) PCT Filed: Mar. 30, 2021

(86) PCT No.: PCT/CN2021/084057

§ 371 (c)(1),
(2) Date: Sep. 22, 2022

(87) PCT Pub. No.: WO2021/197338

PCT Pub. Date: Oct. 7, 2021

(65) Prior Publication Data

US 2023/0119296 A1 Apr. 20, 2023

(30) Foreign Application Priority Data

Mar. 30, 2020 (CN) ........................ 202010236147.6

(51) Int. Cl.
*C07D 401/12* (2006.01)

(52) U.S. Cl.
CPC ........ *C07D 401/12* (2013.01); *C07B 2200/13* (2013.01)

(58) Field of Classification Search
CPC .......................... C07D 401/12; C07B 2200/13
(Continued)

(56) References Cited

U.S. PATENT DOCUMENTS 4,749,406 A 6/1988 Ciba-Geigy
12,152,048 B2 * 11/2024 Deng et al. ............... C07F 9/60
(Continued)

FOREIGN PATENT DOCUMENTS

CN 102239149 A 11/2011
CN 103906744 A * 7/2014 ......... A61K 31/4709
(Continued)

OTHER PUBLICATIONS

CN106632255A, Translation, Clarivate Analytics, p. 1-20 (Year: 2017).*
(Continued)

*Primary Examiner* — Jeffrey S Lundgren
*Assistant Examiner* — Heather Dahlin
(74) *Attorney, Agent, or Firm* — Ice Miller LLP

(57) ABSTRACT

The present invention relates to a crystal form of a nitroxoline prodrug, a pharmaceutical composition containing same, and a preparation method therefor and an application thereof. An X-ray powder diffraction pattern of a crystal form A comprises characteristic peaks at 5.74±0.2°, 6.78±0.2°, 10.86±0.2°, 13.54±0.2°, 16.70±0.2°, and 22.65±0.2°; an X-ray powder diffraction pattern of a crystal form B comprises characteristic peaks at 5.44±0.2°, 10.90±0.2°, 14.09±0.2°, 16.17±0.2°, 17.92±0.2°, 20.66±0.2°, and 23.13±0.2°. Compared with nitroxoline, the
(Continued)

crystal forms A and the B in the present application are not prone to staining, have low requirements for equipment, and are more suitable for industrial production; the stable properties are more conducive to quality control on industrial production and stability in drug efficacy.

25 Claims, 4 Drawing Sheets

(58) Field of Classification Search
USPC .......................................................... 514/314
See application file for complete search history.

(56) References Cited

U.S. PATENT DOCUMENTS

2004/0186139 A1* 9/2004 Reddy et al. ...... A61K 31/4439 514/338
2016/0175305 A1* 6/2016 Feng et al. ........... A61K 31/506
2019/0350920 A1* 11/2019 Luke et al. ........ A61K 31/4709

FOREIGN PATENT DOCUMENTS

| | | | | | |
|---|---|---|---|---|---|
| CN | 106632255 | A | * | 5/2017 | ........... C07D 401/12 |
| CN | 110343090 | A | * | 10/2019 | ........... C07D 401/12 |
| CN | 111514142 | A | | 8/2020 | |
| CN | 111646936 | A | | 9/2020 | |
| WO | 2011150338 | A1 | | 12/2011 | |
| WO | 2020063824 | A1 | | 4/2020 | |

OTHER PUBLICATIONS

CN-110343090-A, Translation, Clarivate Analytics, p. 1-142 (Year: 2019).*
CN 103906744 A, Translation, Clarivate analytics (Year: 2014).*
International Search Report issued Jun. 22, 2021 in PCT/CN2021/084057.

* cited by examiner

CRYSTAL FORM OF NITROXOLINE PRODRUG, PHARMACEUTICAL COMPOSITION CONTAINING SAME, AND PREPARATION METHOD THEREFOR AND APPLICATION THEREOF

CROSS-REFERENCE TO RELATED APPLICATION

This application is a Section 371 of International Application No. PCT/CN2021/084057 filed Mar. 30, 2021, which was published in the Chinese language Oct. 7, 2021, under International Publication No. WO 2021/197338 A1, which claims priority to Chinese Patent Application No. 202010236147.6 filed Mar. 30, 2020, the disclosures of which are incorporated herein by reference in their entireties.

FIELD OF THE INVENTION

The present invention relates to a crystal form of a nitroxoline prodrug, a pharmaceutical composition containing same, and a preparation method therefor and an application thereof.

BACKGROUND OF THE INVENTION

Nitroxoline, a commercially available antibacterial drug, has long been used in the treatment of urinary tract infections. Recent discoveries have shown that nitroxoline is also very effective in inhibiting angiogenesis and inhibiting the growth and invasion of cancer cells, and is currently being developed for anti-tumor applications.

Human pharmacokinetic studies have shown that nitroxoline can be rapidly absorbed into the blood circulation. However, due to the severe first-pass effect of the liver on the drug, its biological half-life is very short (a single-arm, open-label, multi-center phase II clinical trial conducted by Jiangsu Yahong Meditech Co., Ltd. in China has shown that its half-life is 1.22-1.44 hours), thus frequent administration is required. In order to maintain continuous drug exposure, nitroxoline drugs are generally prescribed to be administered three times a day (TID) or four times a day (QID), which not only brings economic losses, is not conducive to patient compliance, but increases the persistent damage of the drug to the body as a more severe consequence. Meanwhile, due to the very low water solubility of nitroxoline, it is often necessary to prepare it as an immediate-release formulation to improve the solubility, which virtually increases the production cost.

A prodrug is a compound obtained by chemical modification of an active drug, which is converted into the original drug in vivo by the action of enzymes to exert its efficacy. Prodrugs are widely used in drug research and development, and they have been successfully developed for many different drugs with good effects in application. The prodrug strategy can solve some defects of the active agent due to its own physical and chemical properties, for example: 1) eliminating the bad odor of the drug; 2) increasing the blood concentration of the drug; 3) improving the lipid solubility or water solubility of the drug; 4) prolonging the action time of the drug; 5) changing the administration route of the drug, and the like.

The polymorphism of drugs have become an indispensable and important part in drug research and development and drug quality control. The research on drug polymorphism facilitates the selection of the biological activity of the drug compound, and helps to improve drug stability, solubility and other properties, which in turn is beneficial to the development of drug preparations, as well as the storage of drugs, the improvement of the quality of drug production, and the like. It can also improve the bioavailability of compounds and enhance the clinical efficacy.

However, there is no relevant report of nitroxoline prodrugs and crystal forms thereof in the prior art.

SUMMARY OF THE INVENTION

The technical problem solved by the present invention is to provide a crystal form of a nitroxoline prodrug, a pharmaceutical composition containing same, and a preparation method therefor and an application thereof.

The inventor has studied a large number of nitroxoline prodrugs (especially the nitroxoline prodrug compounds described in the examples of WO2020/063824), and has found that ((5-nitroquinolin-8-yl)oxy)methyl-isobutyryl-L-prolinate, a nitroxoline prodrug, has better water solubility, gastrointestinal stability and pharmacokinetics than other compounds. Further, the inventor has found that the amorphous form of ((5-nitroquinolin-8-yl)oxy)methyl-isobutyryl-L-prolinate has poor stability, which is not conducive to the preparation of formulations. On this basis, through further research, the inventor has obtained the crystal forms of the present invention and the preparation method therefor.

The present invention provides crystal form A of ((5-nitroquinolin-8-yl)oxy)methyl-isobutyryl-L-prolinate, wherein the X-ray powder diffraction pattern thereof, which is obtained by using Cu-Kα irradiation and expressed in 2θ angle, comprises characteristic peaks at 5.74±0.2°, 6.78±0.2°, 10.86±0.2°, 13.54±0.2°, 16.70±0.2° and 22.65±0.2°.

In some preferred embodiments, the X-ray powder diffraction pattern of the crystal form A of ((5-nitroquinolin-8-yl)oxy)methyl-isobutyryl-L-prolinate, which is obtained by using Cu-Kα irradiation and expressed in 2θ angle, comprises characteristic peaks at 5.74±0.2°, 6.78±0.2°, 8.25±0.2°, 10.86±0.2°, 13.54±0.2°, 14.92±0.2°, 16.70±0.2°, 17.23±0.2°, 18.10±0.2°, 19.56±0.2°, 22.65±0.2° and 27.22±0.2°.

In some preferred embodiments, the X-ray powder diffraction pattern of the crystal form A of ((5-nitroquinolin-8-yl)oxy)methyl-isobutyryl-L-prolinate, which is obtained by using Cu-Kα irradiation and expressed in 2θ angle, is as shown in FIG. 1.

In some preferred embodiments, the differential scanning calorimetry of the crystal form A shows an endothermic peak at 101.4° C.

In some preferred embodiments, the differential scanning calorimetry of the crystal form A of ((5-nitroquinolin-8-yl)oxy)methyl-isobutyryl-L-prolinate shows an endothermic peak at 101.4° C.

The present invention also provides a method for preparing the aforementioned crystal form A of ((5-nitroquinolin-8-yl)oxy)methyl-isobutyryl-L-prolinate, comprising the following steps of:

mixing Solution I containing ((5-nitroquinolin-8-yl)oxy)methyl-isobutyryl-L-prolinate and a positive solvent with an anti-solvent to precipitate a solid, and performing solid-liquid separation to obtain the crystal form A.

In the above preparation method, the positive solvent can be a benign solvent capable of dissolving ((5-nitroquinolin-8-yl)oxy)methyl-isobutyryl-L-prolinate. The positive solvent is preferably one or more of ester solvent, $C_1$-$C_6$ alcohol solvent, ketone solvent, nitrile solvent, ether solvent and lower halogenated alkane solvent.

Wherein, the ester solvent is preferably ethyl acetate.

Wherein, the $C_1$-$C_6$ alcohol solvent is preferably one or more of methanol, ethanol, isopropanol and isobutanol, more preferably methanol and/or ethanol, and further more preferably methanol or ethanol.

Wherein, the ketone solvent is preferably one or more of acetone, methyl ethyl ketone and methyl isobutyl ketone, more preferably acetone or methyl isobutyl ketone, and further more preferably acetone.

Wherein, the nitrile solvent is preferably acetonitrile.

Wherein, the ether solvent is preferably tetrahydrofuran and/or 1,4-dioxane, and more preferably tetrahydrofuran.

Wherein, the lower halogenated alkane solvent is preferably dichloromethane.

Wherein, the positive solvent is more preferably an ester solvent, wherein the ester solvent is preferably a $C_1$-$C_5$ ester solvent, and more preferably ethyl acetate.

In the above preparation method, preferably after filtration, Solution I is obtained.

In the above preparation method, the anti-solvent can be a poor solvent capable of promoting the crystallization or precipitation of ((5-nitroquinolin-8-yl)oxy)methyl-isobutyryl-L-prolinate in Solution I. The anti-solvent is preferably one or more of ether solvent, alcohol, lower alkane solvent and water, and more preferably one or more of ether solvent, lower alkane solvent and water.

Wherein, the ether solvent is preferably one or more of methyl tert-butyl ether, diethyl ether and petroleum ether, more preferably petroleum ether and/or methyl tert-butyl ether, and further more preferably petroleum ether or methyl tert-butyl ether.

Wherein, the alcohol is preferably a $C_1$-$C_6$ alcohol, and more preferably isopropanol.

Wherein, the lower alkane solvent is preferably one or more of n-heptane, n-hexane and n-octane, and more preferably n-heptane.

Wherein, the anti-solvent is more preferably an ether solvent, wherein the ether solvent is preferably petroleum ether.

In particular, in the above preparation method, the positive solvent is more preferably an ester solvent, wherein the ester solvent is preferably a $C_1$-$C_5$ ester solvent, more preferably ethyl acetate; and the anti-solvent is more preferably an ether solvent, wherein the ether solvent is preferably petroleum ether.

In the above preparation method, the volume ratio of the positive solvent to the anti-solvent is preferably 1:20 to 2:1, more preferably 1:10 to 1:2, for example 1:5 or 1:9, and even more preferably 0.3-0.5.

In the above preparation method, the mixing can be achieved by stirring.

In the above preparation method, the temperature of mixing can be room temperature.

In the above preparation method, the temperature of solid precipitation can be room temperature.

The present invention also provides a second method for preparing the aforementioned crystal form A of ((5-nitroquinolin-8-yl)oxy)methyl-isobutyryl-L-prolinate, comprising the following steps of:

mixing Solution II containing ((5-nitroquinolin-8-yl)oxy)methyl-isobutyryl-L-prolinate and a solvent at room temperature to 50° C., and performing centrifugation to obtain the crystal form A;

the solvent is one or more of $C_1$-$C_6$ alcohol solvent, ester solvent, ether solvent, lower alkane solvent, lower halogenated alkane solvent, ketone solvent, aromatic hydrocarbon solvent, nitrile solvent, dimethyl sulfoxide and water, and preferably one or more of $C_1$-$C_6$ alcohol solvent, ester solvent, ether solvent, lower alkane solvent, ketone solvent, aromatic hydrocarbon solvent, nitrile solvent, dimethyl sulfoxide and water.

Wherein, the $C_1$-$C_6$ alcohol solvent is preferably one or more of methanol, ethanol and isopropanol, and more preferably isopropanol and/or methanol.

Wherein, the ester solvent is preferably one or more of methyl acetate, ethyl acetate and isopropyl acetate, and more preferably isopropyl acetate and/or ethyl acetate.

Wherein, the ether solvent is preferably one or more of methyl ethyl ether, diethyl ether, methyl isopropyl ether, methyl tert-butyl ether, cyclopentyl methyl ether, anisole, tetrahydrofuran, 2-methyltetrahydrofuran and 1,4-dioxane, and more preferably one or more of methyl tert-butyl ether, cyclopentyl methyl ether, anisole, tetrahydrofuran, 2-methyltetrahydrofuran and 1,4-dioxane.

Wherein, the lower alkane solvent is preferably n-heptane.

Wherein, the lower halogenated alkane solvent is preferably dichloromethane.

Wherein, the ketone solvent is preferably one or more of methyl ethyl ketone, methyl isobutyl ketone and acetone.

Wherein, the aromatic hydrocarbon solvent is preferably toluene.

Wherein, the nitrile solvent is preferably acetonitrile.

In some preferred embodiments, in the second preparation method as described above, the solvent is a mixed solvent of $C_1$-$C_6$ alcohol and water, a mixed solvent of ether and lower alkane, a mixed solvent of ketone and lower alkane, a mixed solvent of ketone and ether, a mixed solvent of ester and $C_1$-$C_6$ alcohol, a mixed solvent of aromatic hydrocarbon and lower alkane, a mixed solvent of ketone and $C_1$-$C_6$ alcohol or a mixed solvent of ether and ester, preferably a mixed solvent of $C_1$-$C_6$ alcohol and water, and more preferably a mixed solvent of isopropanol and water or methanol and water;

the volume ratio of the former to the latter in the mixed solvent is preferably 1:8-1:1, and more preferably 1:4-1:2.

In some preferred embodiments, in the second preparation method as described above, wherein:

any crystal form or amorphous form of ((5-nitroquinolin-8-yl)oxy)methyl-isobutyryl-L-prolinate is suspended in a solvent at a temperature of 50° C., stirred and centrifuged to obtain the crystal form A;

the solvent is one or more of $C_1$-$C_6$ alcohol solvent, ester solvent, ketone solvent, ether solvent, lower alkane solvent, aromatic hydrocarbon solvent, nitrile solvent and water, preferably a mixed solvent of two solvents, more preferably a mixed solvent of $C_1$-$C_6$ alcohol and water, a mixed solvent of ketone and ether, a mixed solvent of ester and $C_1$-$C_6$ alcohol, a mixed solvent of ketone and $C_1$-$C_6$ alcohol, a mixed solvent of ether and ester, a mixed solvent of aromatic hydrocarbon and lower alkane, a mixed solvent of ether and lower alkane, a mixed solvent of two ethers or a mixed solvent of nitrile and ether, and further preferably a mixed solvent of isopropanol/water, methyl isobutyl ketone/methyl tert-butyl ether, ethyl acetate/isopropanol, toluene/n-heptane, 2-methyltetrahydrofuran/n-heptane, butanone/isopropanol, acetonitrile/cyclopentyl methyl ether, anisole/isopropyl isopropyl acetate or 1,4-dioxane/cyclopentyl methyl ether;

the volume ratio of the former to the latter in the mixed solvent is preferably 1:4 to 1:2.

The present invention also provides a third method for preparing the aforementioned crystal form A of ((5-nitroquinolin-8-yl)oxy)methyl-isobutyryl-L-prolinate, comprising the following steps of:

placing Solution III containing ((5-nitroquinolin-8-yl)oxy)methyl-isobutyryl-L-prolinate and a solvent in a cycle of 50° C.→5° C.→50° C. for one to five cycles, preferably for three cycles, until solid precipitation, and performing solid-liquid separation to obtain the crystal form A; or, heating Solution III to 50° C. for dissolving, performing hot filtration, cooling the filtrate to 5° C. to −20° C., and performing solid-liquid separation to obtain the crystal form A;

the solvent is preferably one or more, preferably one or two, of $C_1$-$C_6$ alcohol solvent, ester solvent, ketone solvent, ether solvent, lower alkane solvent, aromatic hydrocarbon solvent and water.

Wherein, the $C_1$-$C_6$ alcohol solvent is preferably one or more of methanol, ethanol and isopropanol.

Wherein, the ester solvent is preferably one or more of methyl acetate, ethyl acetate and isopropyl acetate.

Wherein, the ketone solvent is preferably one or more of methyl ethyl ketone, methyl propyl ketone and acetone.

Wherein, the ether solvent is preferably one or more of methyl ethyl ether, diethyl ether, methyl isopropyl ether, methyl tert-butyl ether, cyclopentyl methyl ether and anisole.

Wherein, the lower alkane solvent is preferably n-heptane.

Wherein, the aromatic hydrocarbon solvent is preferably toluene.

In some preferred embodiments, in the third preparation method as described above, wherein the solvent is a mixed solvent of $C_1$-$C_6$ alcohol and water, a mixed solvent of $C_1$-$C_6$ alcohol and ether, a mixed solvent of ketone and ester, a mixed solvent of aromatic hydrocarbon and ester or a mixed solvent of ketone and lower alkane; the $C_1$-$C_6$ alcohol solvent is preferably ethanol and/or isopropanol, the ketone solvent is preferably butanone and/or methyl isobutyl ketone; the ester solvent is preferably isopropyl acetate; the ether solvent is preferably cyclopentyl methyl ether; the aromatic hydrocarbon solvent is preferably toluene; the lower alkane solvent is preferably n-heptane;

the volume ratio of the former to the latter in the mixed solvent is preferably 1:20 to 2:1, and more preferably 1:10 to 1:2.

The present invention also provides a fourth method for preparing the aforementioned crystal form A of ((5-nitroquinolin-8-yl)oxy)methyl-isobutyryl-L-prolinate, comprising the following steps of:

placing an open first container with any crystal form or amorphous form of ((5-nitroquinolin-8-yl)oxy)methyl-isobutyryl-L-prolinate solid in a second container with a solvent, sealing the second container, leaving it to stand at room temperature, and collecting the product when it is observed that the solid becomes wet or there is solid precipitation to obtain the crystal form A; wherein, the solvent is one or more of $C_1$-$C_6$ alcohol solvent, ether solvent, ketone solvent, ester solvent, aromatic hydrocarbon solvent, dimethyl sulfoxide and water.

Wherein, the $C_1$-$C_6$ alcohol solvent is preferably one or more of methanol, ethanol, isopropanol and isobutanol, and more preferably ethanol and/or isopropanol.

Wherein, the ether solvent is preferably one or more of methyl tert-butyl ether, tetrahydrofuran, 2-methyltetrahydrofuran, 1,4-dioxane and anisole, and more preferably tetrahydrofuran.

Wherein, the ketone solvent is preferably one or more of acetone, methyl ethyl ketone and methyl isobutyl ketone, and more preferably acetone.

Wherein, the ester solvent is preferably ethyl acetate.

Wherein, the aromatic hydrocarbon solvent is preferably toluene.

The present invention also provides a fifth method for preparing the aforementioned crystal form A of ((5-nitroquinolin-8-yl)oxy)methyl-isobutyryl-L-prolinate, comprising the following steps of:

placing an open first container with Solution IV containing ((5-nitroquinolin-8-yl)oxy)methyl-isobutyryl-L-prolinate and a positive solvent in a second container with an anti-solvent, sealing the second container, leaving it to stand at room temperature, and collecting the product when it is observed that the solid becomes wet or there is solid precipitation to obtain the crystal form A;

wherein, the positive solvent is preferably one or more of $C_1$-$C_6$ alcohol solvent, ether solvent and ketone solvent; the anti-solvent is one or more of lower alkane solvent, ether solvent, alcohol solvent and water.

As the positive solvent, the $C_1$-$C_6$ alcohol solvent is preferably one or more of methanol, ethanol, isopropanol and isobutanol, and more preferably ethanol.

As the positive solvent, the ether solvent is preferably one or more of tetrahydrofuran, 2-methyltetrahydrofuran and 1,4-dioxane, and more preferably 1,4-dioxane.

As the positive solvent, the ketone solvent is preferably one or more of acetone, methyl ethyl ketone and methyl isobutyl ketone, and more preferably methyl isobutyl ketone.

As the anti-solvent, the lower alkane solvent is preferably n-heptane.

As the anti-solvent, the ether solvent is preferably methyl tert-butyl ether.

As the anti-solvent, the alcohol solvent is preferably isopropanol.

In some preferred embodiments, in the fifth preparation method as described above, the volume ratio of the positive solvent to the anti-solvent is preferably 1:20 to 2:1, and more preferably 1:10 to 1:2, for example 1:8 or 1:4.

The present invention also provides a sixth method for preparing the aforementioned crystal form A of ((5-nitroquinolin-8-yl)oxy)methyl-isobutyryl-L-prolinate, comprising the following steps of:

volatilizing Solution V containing ((5-nitroquinolin-8-yl)oxy)methyl-isobutyryl-L-prolinate and a solvent at room temperature, and collecting the precipitated solid to obtain the crystal form A;

the solvent is one or more of $C_1$-$C_6$ alcohol solvent, ketone solvent, ester solvent, ether solvent, lower alkane solvent, aromatic hydrocarbon solvent, nitrile solvent, lower halogenated alkane solvent and water, and preferably one or more of $C_1$-$C_6$ alcohol solvent, ketone solvent, ether solvent and lower halogenated alkane solvent.

Wherein, the $C_1$-$C_6$ alcohol solvent is preferably one or more of methanol, ethanol and isopropanol, and more preferably isopropanol.

Wherein, the ketone solvent is preferably one or more of methyl ethyl ketone, methyl isobutyl ketone and acetone, and more preferably methyl ethyl ketone and/or methyl isobutyl ketone.

Wherein, the ester solvent is preferably one or more of methyl acetate, ethyl acetate and isopropyl acetate.

Wherein, the ether solvent is preferably one or more of methyl ethyl ether, diethyl ether, methyl isopropyl ether, methyl tert-butyl ether, cyclopentyl methyl ether, anisole and 1,4-dioxane, and more preferably 1,4-dioxane.

Wherein, the lower alkane solvent is preferably n-heptane.

Wherein, the aromatic hydrocarbon solvent is preferably toluene.

Wherein, the nitrile solvent is preferably acetonitrile.

Wherein, the lower halogenated alkane solvent is preferably dichloromethane.

The present invention also provides crystal form B of ((5-nitroquinolin-8-yl)oxy)methyl-isobutyryl-L-prolinate, wherein the X-ray powder diffraction pattern thereof, which is obtained by using Cu-Kα irradiation and expressed in 2θ angle, comprises characteristic peaks at 5.44±0.2°, 10.90±0.2°, 14.09±0.2°, 16.17±0.2°, 17.92±0.2°, 20.66±0.2° and 23.13±0.2°.

In some preferred embodiments, the X-ray powder diffraction pattern of the crystal form B of ((5-nitroquinolin-8-yl)oxy)methyl-isobutyryl-L-prolinate, which is obtained by using Cu-Kα irradiation and expressed in 2θ angle, comprises characteristic peaks at 5.44±0.2°, 6.19±0.2°, 10.90±0.2°, 14.09±0.2°, 14.88±0.2°, 16.17±0.2°, 17.92±0.2°, 20.66±0.2°, 21.69±0.2° and 23.13±0.2°.

In some preferred embodiments, the X-ray powder diffraction pattern of the crystal form B of ((5-nitroquinolin-8-yl)oxy)methyl-isobutyryl-L-prolinate, which is obtained by using Cu-Kα irradiation and expressed in 2θ angle, comprises characteristic peaks at 5.44±0.2°, 6.19±0.2°, 8.06±0.2°, 10.90±0.2°, 12.18±0.2°, 14.09±0.2°, 14.88±0.2°, 16.17±0.2°, 17.92±0.2°, 20.66±0.2°, 21.69±0.2°, 23.13±0.2°, 24.42±0.2° and 26.03±0.2°.

In some preferred embodiments, the X-ray powder diffraction pattern of the crystal form B of ((5-nitroquinolin-8-yl)oxy)methyl-isobutyryl-L-prolinate, which is obtained by using Cu-Kα irradiation and expressed in 2θ angle, is as shown in FIG. 6.

In some preferred embodiments, the differential scanning calorimetry of the crystal form B of ((5-nitroquinolin-8-yl)oxy)methyl-isobutyryl-L-prolinate shows an endothermic peak at 101.5° C.

The present invention also provides a method for preparing the aforementioned crystal form B of ((5-nitroquinolin-8-yl)oxy)methyl-isobutyryl-L-prolinate, comprising the following steps of:

mixing Solution A containing ((5-nitroquinolin-8-yl)oxy)methyl-isobutyryl-L-prolinate and a positive solvent with an anti-solvent to precipitate a solid, and performing solid-liquid separation to obtain the crystal form B;

the positive solvent is an ester solvent, the ester solvent is preferably one or more of methyl acetate, ethyl acetate and isopropyl acetate, and more preferably ethyl acetate;

the anti-solvent is an alkane solvent, the alkane solvent is preferably one or more of n-hexane, n-heptane and n-octane, and more preferably n-heptane.

In some preferred embodiments, the volume ratio of the positive solvent to the anti-solvent is 1:20 to 2:1, and preferably 1:10 to 1:2.

In some preferred embodiments, the crystal form A of ((5-nitroquinolin-8-yl)oxy)methyl-isobutyryl-L-prolinate is dissolved in a positive solvent to obtain Solution A.

The present invention also provides a pharmaceutical composition comprising the aforementioned crystal form A of ((5-nitroquinolin-8-yl)oxy)methyl-isobutyryl-L-prolinate or the crystal form B of ((5-nitroquinolin-8-yl)oxy)methyl-isobutyryl-L-prolinate and an auxiliary material.

In the aforementioned pharmaceutical composition, the auxiliary material generally refers to a pharmaceutically acceptable carrier, diluent or excipient.

The present invention also provides a use of the aforementioned crystal form A of ((5-nitroquinolin-8-yl)oxy)methyl-isobutyryl-L-prolinate or the crystal form B of ((5-nitroquinolin-8-yl)oxy)methyl-isobutyryl-L-prolinate or a pharmaceutical composition containing same in the preparation of a medicament for treating an infectious disease or a cancer.

Wherein, the infectious disease is preferably systemic infection, reproductive system infection or urinary system infection.

Wherein, the cancer is preferably bladder cancer or prostate cancer.

Herein, the room temperature refers to 10-35° C., and preferably 15-30° C.

Herein, the alcohol solvent refers to a class of organic compounds formed by replacing one or several hydrogens in a hydrocarbon molecule with hydroxyl group(s), usually linear or branched chain alcohol compounds with 1-6 carbons, for example one or more of methanol, ethanol, n-propanol, isopropanol, n-butanol, sec-butanol, primary butanol and tert-butanol.

Herein, the ketone solvent refers to a compound in which a carbonyl group is connected to two alkyl groups, usually a linear or branched chain ketone compound with 1-6 carbons, for example one or more of acetone, butanone (also known as methyl ethyl ketone), methyl isopropyl ketone and methyl isobutyl ketone.

Herein, the ester solvent refers to a compound formed by esterification of inorganic or organic acids and alcohols to remove water, usually a linear or branched chain ester compound with 1-6 carbons, for example one or more of ethyl formate, methyl acetate, ethyl acetate, isopropyl acetate and isobutyl acetate.

Herein, the ether solvent refers to a product in which the hydrogen in the hydroxyl group of alcohol or phenol is substituted by a alkyl group, usually a linear, branched chain or cyclic ether compound with 1-6 carbons, for example one or more of diethyl ether, methyl tert-butyl ether, tetrahydrofuran, 2-methyltetrahydrofuran, 1,4-dioxane and cyclopentyl methyl ether.

Herein, the lower alkane solvent refers to a hydrocarbon that is liquid at room temperature, usually a linear or branched chain alkane or cycloalkane compound with 4-10 carbon atoms, for example one or more of n-pentane, n-heptane, n-octane and cyclohexane.

Herein, the lower halogenated alkane solvent refers to a hydrocarbon compound containing one or more of fluorine, chlorine, bromine and iodine that is liquid at room temperature, usually with 1-10 carbon atoms, preferably a halogen-substituted linear or branched chain alkane compound with 1-6 carbon atoms, for example one or more of dichloromethane, dichloroethane, chloroform, bromoethane and bromobutane.

Herein, the aromatic hydrocarbon solvent refers to a hydrocarbon containing benzene ring structure in its molecule that is liquid at room temperature, for example toluene and/or xylene.

Herein, the nitrile solvent refers to a compound containing a cyano group in the molecule, which usually refers to a linear or branched chain nitrile compound with 1-6 carbons, and preferably acetonitrile.

Herein, amorphous form of ((5-nitroquinolin-8-yl)oxy)methyl-isobutyryl-L-prolinate generally refers to a crude product of amorphous form of ((5-nitroquinoline) olin-8-yl)oxy)methyl-isobutyryl-L-prolinate, of course, it can also be pure ((5-nitroquinolin-8-yl)oxy)methyl-isobutyryl-L-prolinate.

Herein, Solution I can be a solution prepared from any crystal form or amorphous form of ((5-nitroquinolin-8-yl)oxy)methyl-isobutyryl-L-prolinate, and a positive solvent.

Herein, Solution II can be a solution prepared from any crystal form or amorphous form of ((5-nitroquinolin-8-yl)oxy)methyl-isobutyryl-L-prolinate, and a solvent.

Herein, Solution III can be a solution prepared from any crystal form or amorphous form of ((5-nitroquinolin-8-yl)oxy)methyl-isobutyryl-L-prolinate, and a solvent.

Herein, Solution IV can be a solution prepared from any crystal form or amorphous form of ((5-nitroquinolin-8-yl)oxy)methyl-isobutyryl-L-prolinate, and a positive solvent.

Herein, Solution V can be a solution prepared from any crystal form or amorphous form of ((5-nitroquinolin-8-yl)oxy)methyl-isobutyryl-L-prolinate, and a solvent.

Herein, Solution A can be a solution prepared from any crystal form or amorphous form of ((5-nitroquinolin-8-yl)oxy)methyl-isobutyryl-L-prolinate, and a positive solvent.

Herein, the positive solvent refers to a benign solvent capable of dissolving ((5-nitroquinolin-8-yl)oxy)methyl-isobutyryl-L-prolinate. The positive solvent is preferably one or more of ester solvent, $C_1$-$C_6$ alcohol solvent, ketone solvent, nitrile solvent, ether solvent and lower halogenated alkane solvent.

Herein, the anti-solvent refers to a poor solvent capable of promoting the crystallization or precipitation of ((5-nitroquinolin-8-yl)oxy)methyl-isobutyryl-L-prolinate in the solution. The anti-solvent is preferably one or more of ether solvent, lower alkane solvent and water.

"Pharmaceutically acceptable" as described herein is one which is useful for preparing a pharmaceutical composition that is generally safe, have neither biological toxicity nor other undesirable toxicity, and are acceptable for veterinary use and human pharmaceutical use.

"Carrier" as described herein refers to a diluent, adjuvant or excipient administered together with the compound. The pharmaceutically acceptable carrier can be a liquid, for example water and oil, including petroleum, oils of animal, plant or synthetic origin, for example peanut oil, soybean oil, mineral oil, rapeseed oil, and the like. The pharmaceutically acceptable carrier can also be physiological saline, gum arabic, gelatin, starch paste, talc, keratin, silica gel, urea and the like. In addition, an aid, stabilizer, thickener, lubricant, colorant, and the like can also be used.

Those skilled in the art are able to understand that the pharmaceutical composition of the present invention can be formulated according to the specific administration route into various formulations well-known in the art, for example oral formulations (powder, tablet, capsule, soft capsule, liquid medicine, syrup, elixir, pulvis, sachet, granule), or formulations for topical administration (cream, ointment, lotion, gel, balm, plaster, paste, spray, aerosol, and the like), or formulations for injection (solution, suspension, emulsion). In the pharmaceutical compositions according to the present invention, mention may notably be made of those suitable for oral, parenteral (intravenous or subcutaneous) or nasal administration, for example, tablet or dragee, sublingual tablet, gelatin capsule, lozenge, suppository, cream, ointment, skin gel, injection, drinkable suspension, and the like.

The pharmaceutical composition according to the present invention can comprise a pharmaceutically acceptable carrier, adjuvant or diluent, for example a filler, disintegrant, lubricant, suspending agent, binder, sweetener, flavoring agent, preservative, matrix, and the like. The filler is for example starch, pregelatinized starch, lactose, mannitol, chitin, microcrystalline cellulose, sucrose, and the like; the disintegrant is for example starch, pregelatinized starch, microcrystalline cellulose, sodium carboxymethyl starch, cross-linked polyvinylpyrrole, low-substituted hydroxypropyl cellulose, cross-linked sodium carboxymethyl cellulose, and the like; the lubricant is for example magnesium stearate, sodium lauryl sulfate, talc, silicon dioxide, and the like; the suspending agent is for example polyvinylpyrrolidone, microcrystalline cellulose, sucrose, agar, hydroxypropyl methylcellulose, and the like; the binder is for example starch slurry, polyvinylpyrrolidone, hydroxypropyl methylcellulose, and the like. The composition of the present invention can be prepared by any method known in the art, so as to provide rapid, sustained or slow release of the active ingredient after administration to a patient.

The pharmaceutical composition of the present invention is administered to an individual animal such as mammal (rat, mouse, domesticated animal or human) by various routes, all the administration routes are contemplated, for example, the administration route can be oral, topical, rectal administration or intravenous, intramuscular, transdermal, intrathecal, epidural or intraventricular injection.

The administration dosage of the active ingredient of the present invention can vary according to the condition and weight of the individual, the nature and severity of the disease, the form of drug, the administration route, and the administration period, and can also be selected by those skilled in the art. The dose can vary from 1 to 1500 mg/day, and the drug can be administered daily in a single dose or in divided doses.

The positive improvement effect of the present invention is that: in prior art, the nitroxoline API is dark yellow in color, is prone to staining, has high requirements for industrial equipment in the production process and is difficult to clean. Compared with nitroxoline, the crystal form A of ((5-nitroquinolin-8-yl)oxy)methyl-isobutyryl-L-prolinate or the crystal form B of ((5-nitroquinolin-8-yl)oxy)methyl-isobutyryl-L-prolinate prepared in the present invention is not prone to staining, has low requirements for equipment, and is more suitable for industrial production. In addition, the crystal form A and crystal form B prepared in the present invention have stable properties, which are more conducive to quality control on industrial production and stability in drug efficacy. Further, compared with the crystal form B, the crystal form A has more stable properties, and is more conducive to quality control on industrial production and stability in drug efficacy.

DETAILED DESCRIPTION OF THE INVENTION

Figure 1:
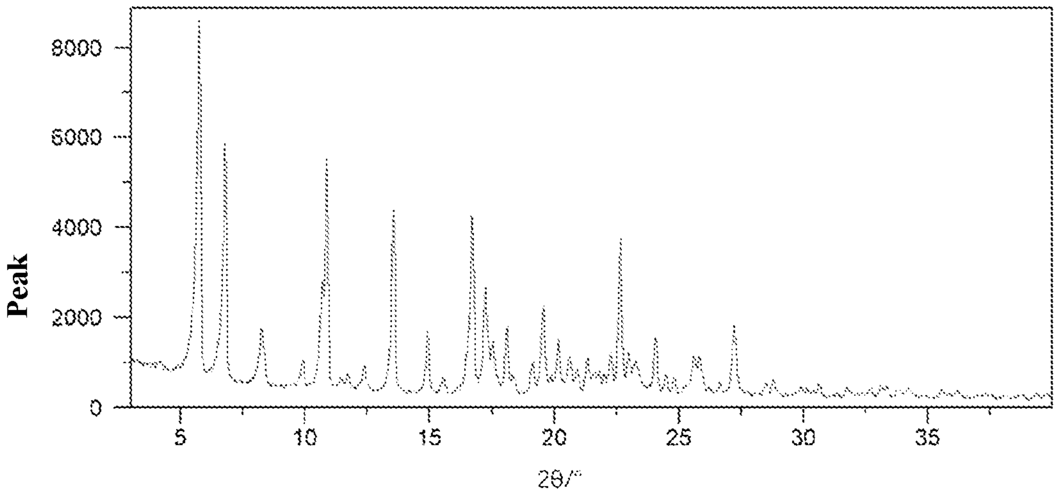
FIG. 1 is a XRPD pattern of crystal form A prepared in Example 2.

The present invention will be described in more detail below with reference to the examples. The examples of the present invention are only used to illustrate the technical solutions of the present invention, but do not limit the essence and scope of the present invention.

In the following examples, the structures of the compounds were identified by nuclear magnetic resonance (NMR) or/and mass spectrometry (MS). The NMR shifts (δ) are given in the unit of $10^{-6}$ (ppm). The NMR determination was performed with a Bruker 400 M nuclear magnetic resonance spectrometer, and the solvent for determination was deuterated dimethyl sulfoxide (dimethyl sulfoxide-$d_6$).

In the following examples, liquid chromatography-mass spectrometer (Thermo, Ultimate3000/MSQ) was used for the MS determination; Agilent 6250 liquid chromatography-mass spectrometer was used for the LC/MS determination; Yantai Huanghai silica gel of 200-300 mesh was generally used as carrier for the silica gel column chromatography.

In the following examples, nitroxoline and L-Boc proline were purchased from Accela Chemical Reagent Co., Ltd.

Experimental Instruments

1. X-ray Powder Diffraction (XRPD)
   Instrument model: Empyrean;
   X-ray: Cu, kα, Kα1 (Å): 1.540598; Kα2 (Å): 1.544426; Kα2/Kα1 intensity ratio: 0.50;
   X-ray tube settings: voltage: 45 kV, current: 40 mA
   Scan mode: continuous
   Scan range (°2Theta): 3-40
   Scan time per step (s): 17.8
   Scan step size (°2TH): 0.0167
   Test time: 5 minutes 30 seconds
2. Thermogravimetric Analysis (TGA)
   Instrument model: TA Q5000/Discovery 5500
   Method: linear heating
   Temperature range: room temperature-350° C.
   Scan rate: 10° C./min
   Shielding gas: nitrogen
   Sample amount: 1-3 mg
3. Differential Scanning Calorimetry (DSC)
   Instrument model: TA Q2000/Discovery 2500
   Method: linear heating
   Temperature range: 25° C.-260° C.
   Scan rate: 10° C./min
   Shielding gas: nitrogen
   Sample amount: 1-3 mg
4. Modulated Differential Scanning Calorimetry (mDSC)
   Test mode: conventional mDSC
   Amplitude (° C.): 1.0
   Modulation period (seconds): 60
   Scan rate (° C./min): 3.0
   Shielding gas: nitrogen
   Sample amount: 1-3 mg
5. Dynamic Vapour Sorption (DVS)

The DVS curves were acquired on DVS Intrinsic of SMS (Surface Measurement Systems). The relative humidity at 25° C. was corrected for the deliquescence points of LiCl, $Mg(NO_3)_2$ and KCl.

Test temperature: 25° C.

Sample amount: 10-20 mg

Shielding gas and flow: nitrogen, 200 mL/min dm/dt: 0.002%/min;

Minimum dm/dt equilibration time: 10 min

Maximum equilibration time: 180 min

RH range: 0% RH-95% RH-0% RH

RH gradient: 10%

6. Polarizing Light Microscope (PLM)

Acquisition was performed by Axio Scope A1 microscope at room temperature.

Example 1 Preparation of ((5-nitroquinolin-8-yl) oxy)methyl-isobutyryl-L-prolinate

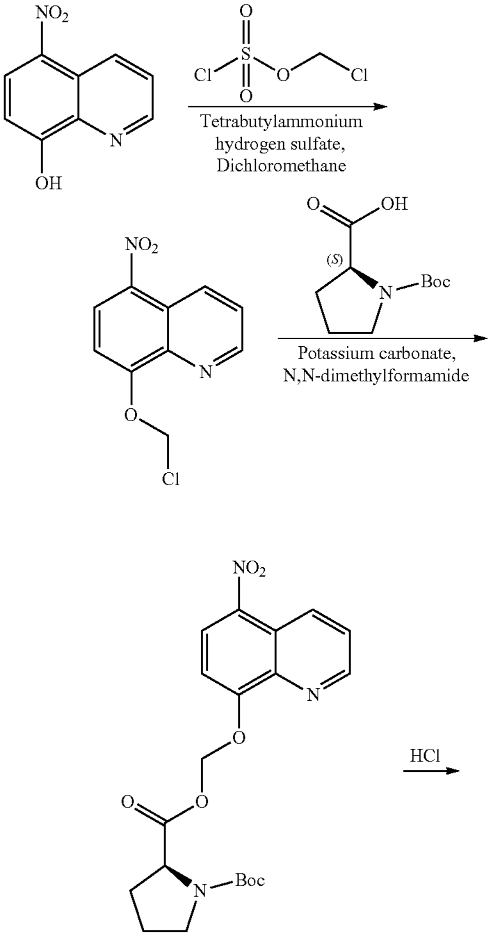

-continued

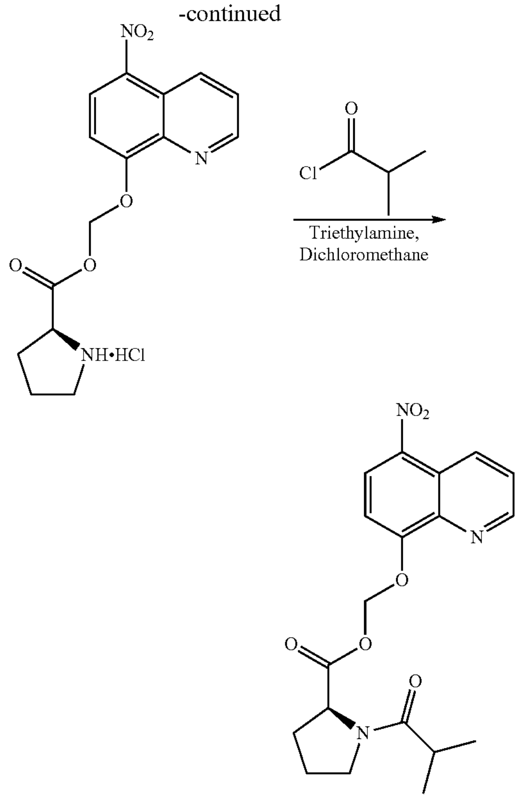

Step 1: Preparation of 5-nitro-8-chloromethoxyquinoline

An aqueous solution of sodium bicarbonate (60 mL, 3.5 mol/L) and tetrabutylammonium hydrogen sulfate (1.78 g, 5.24 mmol) were added to a solution of nitroxoline (10.00 g, 52.59 mmol) in dichloromethane (100 mL) at room temperature. The reaction system was stirred at room temperature for 20 minutes. Chloromethyl chlorosulfonate (10.42 g, 63.15 mmol) was added dropwise to the reaction system, which was then stirred at room temperature for 16 hours. The reaction solution was filtered, and the organic phase was separated, washed successively with a saturated solution of potassium carbonate and saturated brine, dried over anhydrous sodium sulfate, filtered and concentrated under reduced pressure. The residue was purified by silica gel column chromatography (eluent: dichloromethane) to obtain 5-nitro-8-chloromethoxyquinoline (2.5 g, 20% yield).

Step 2: Preparation of 1-(tert-butyl) 2-(((5-nitroquinolin-8-yl)oxy)methyl) (S)-pyrrolidine-1,2-dicarboxylate 8-Chloromethoxy-5-nitroquinoline (1.5 g, 6.3 mmol) and L-Boc proline (2.02 g, 9.4 mmol) were dissolved in 15 mL of DMF at room temperature, and potassium carbonate (1.73 g, 12.6 mmol) was added. The reaction solution was stirred at room temperature for 3 hours, 70 mL of water was added, and the reaction solution was extracted with ethyl acetate (50 mL×2). The organic phase was washed with saturated brine, dried over anhydrous sodium sulfate, filtered and concentrated under reduced pressure to obtain the crude product. The crude product was purified by silica gel column chromatography (PE:EA=1:1) to obtain the product 1-(tert-butyl) 2-(((5-nitroquinolin-8-yl)oxy)methyl) (S)-pyrrolidine-1,2-dicarboxylate (2.6 g, 98% yield).

Step 3: Preparation of ((5-nitroquinolin-8-yl)oxy)methyl L-prolinate hydrochloride 1-(Tert-butyl) 2-(((5-nitroquinolin-8-yl)oxy)methyl) (S)-pyrrolidine-1,2-dicarboxylate (2.6 g, 6.4 mmol) was put into HCl/dioxane (30 mL) at 0° C. and stirred at room temperature for 20 minutes. The reaction solution was concentrated under reduced pressure to obtain the product ((5-nitroquinolin-8-yl)oxy)methyl L-prolinate hydrochloride (2.3 g, 97% yield).

Step 4: Preparation of ((5-nitroquinolin-8-yl)oxy)methyl-isobutyryl-L-prolinate ((5-Nitroquinolin-8-yl)oxy)methyl L-prolinate hydrochloride (150 mg, 0.43 mmol) was added to anhydrous dichloromethane (5 mL) at room temperature. After cooling in an ice bath, isobutyryl chloride (103.7 mg, 0.90 mmol) was added, triethylamine (180 mg, 1.72 mmol) was slowly added dropwise between 0° C. and 10° C., followed by stirring for 20 minutes. The reaction solution was concentrated under reduced pressure, and the residue was purified by silica gel column chromatography (PE:EA=1:1-0:1) to obtain ((5-nitroquinolin-8-yl)oxy)methyl-isobutyryl-L-prolinate (85 mg, 49.3% yield).

$^1$H-NMR (400 MHz, dimethyl sulfoxide-d6): δ: 9.05 (d, J=4.0 Hz, 1H), 9.00 (d, J=8.8 Hz, 1H), 8.56 (d, J=8.8 Hz, 1H), 7.89-7.86 (dd, J=4.0 Hz, 8.8 Hz, 1H), 7.55 (d, J=8.8 Hz, 1H), 6.24-6.11 (m, 2H), 4.36-4.33 (m, 1H), 3.59-3.68 (m, 2H), 2.51-2.66 (m, 1H), 2.14-2.19 (m, 1H), 1.92-1.85 (m, 2H), 1.83-1.78 (m, 1H), 0.95 (d, J=6.8 Hz 0.3H), 0.89 (d, J=6.8 Hz 0.3H).

Calculated MS: 387.3; measured MS: 388.2 $[M+H]^+$.

Example 2 Preparation Example 1 of Crystal Form A of ((5-nitroquinolin-8-yl)oxy)methyl-isobutyryl-L-prolinate 260 g of ((5-nitroquinolin-8-yl)oxy)methyl-isobutyryl-L-prolinate (98.5% purity) prepared according to Example 1 was added to and dissolved in ethyl acetate (800 mL), and filtered through diatomaceous earth to obtain a clear filtrate. The filtrate was concentrated to 400 mL under reduced pressure, and petroleum ether (100 mL) was added under stirring. Stirring was continued at 20-30° C. for 20 minutes until small particles were precipitated out of the solution. Petroleum ether (900 mL) was slowly added dropwise, and a large amount of pale yellow solid was precipitated. Stirring was continued at 20-30° C. for 2 hours, and the reaction solution was filtered to obtain a wet product (300 g) as a pale yellow solid. The wet product was dried under reduced pressure at 30-40° C. to obtain a solid (240 g, 92.3% yield, LCMS purity: 99.6%).

Figure 2:
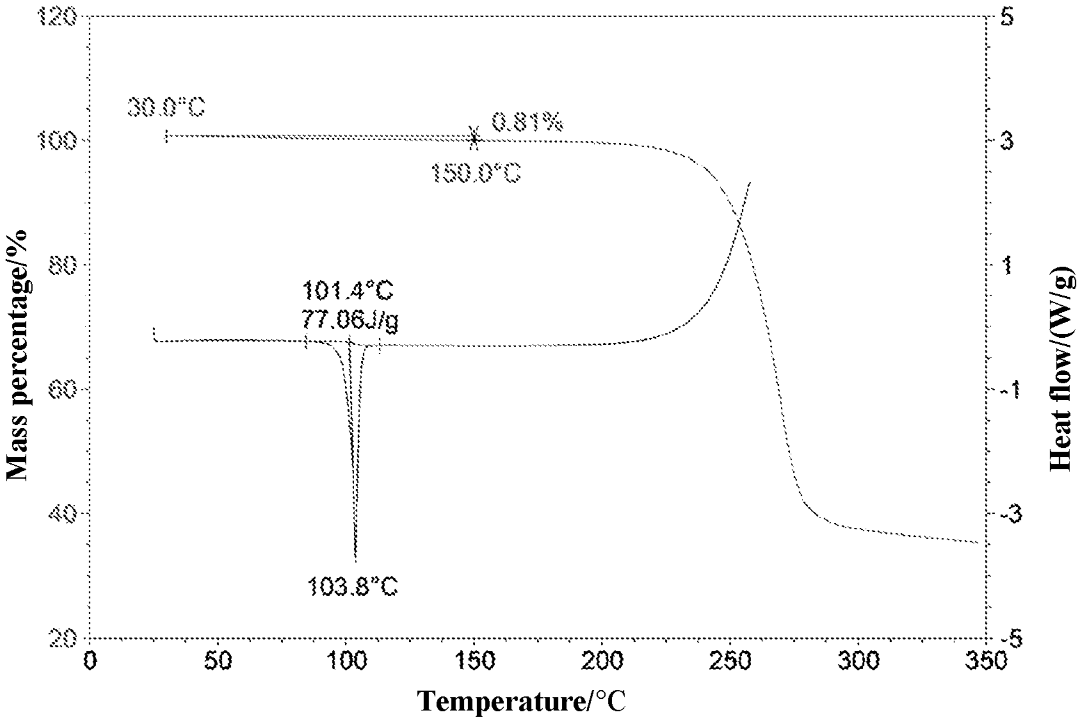
FIG. 2 is a TGA/DSC spectrum of crystal form A prepared in Example 2.
Figure 3:
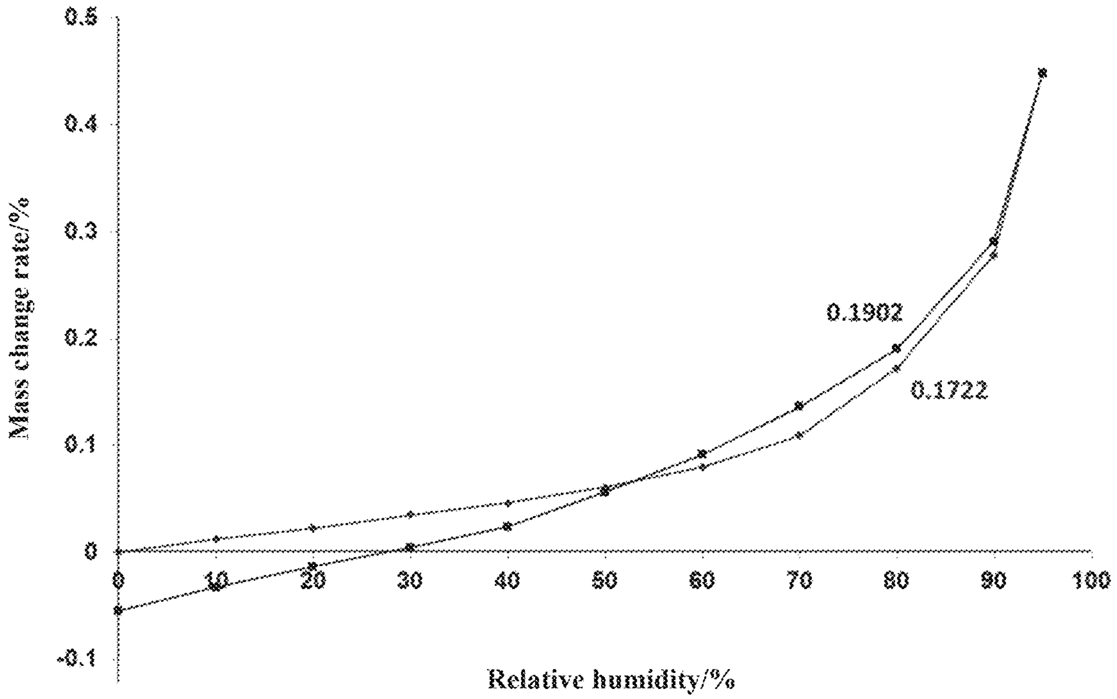
FIG. 3 is a DVS spectrum of crystal form A prepared in Example 2.
Figure 4:
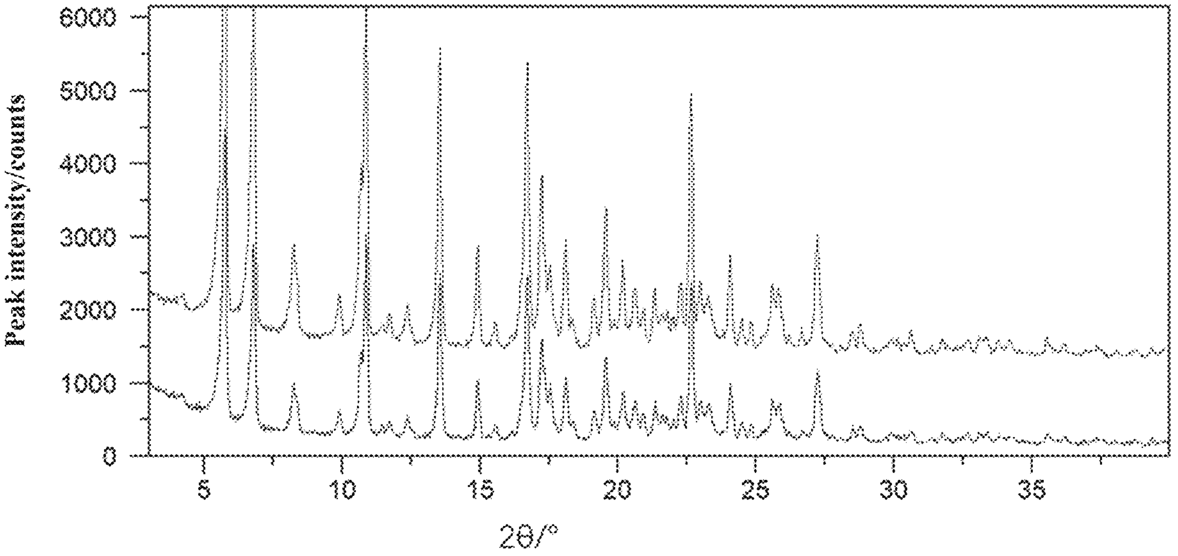
FIG. 4 is a XRPD comparison pattern of crystal form A prepared in Example 2 before and after the DVS test.
Figure 5:
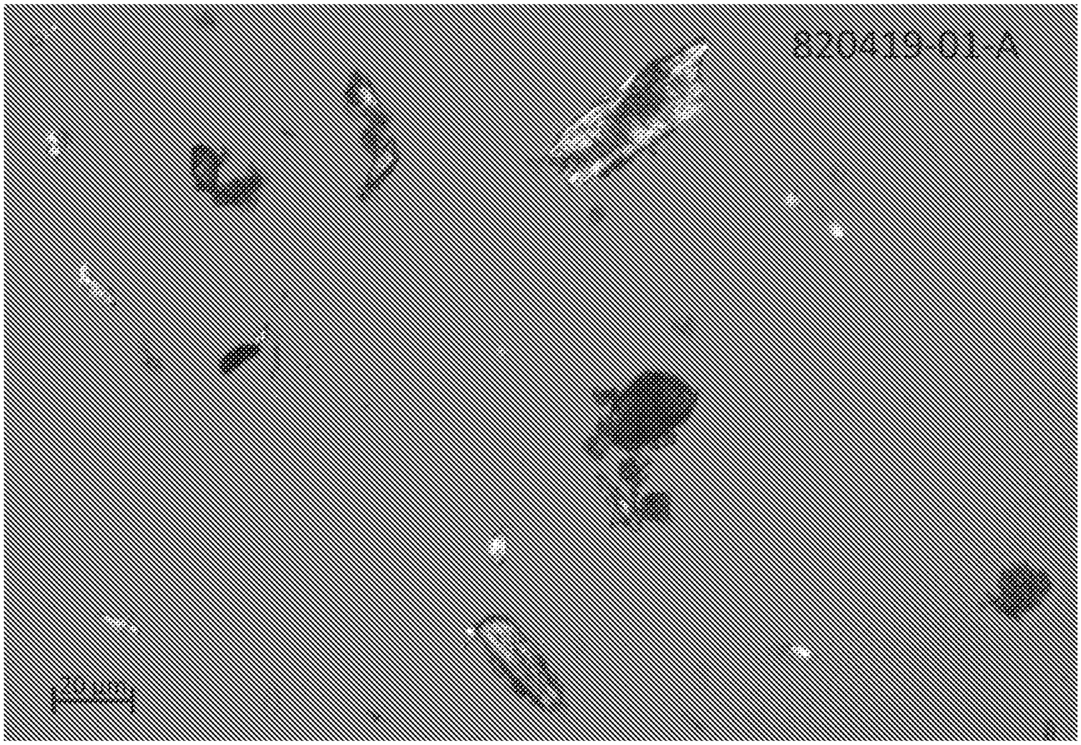
FIG. 5 is a PLM photograph of crystal form A prepared in Example 2.

The X-ray powder diffraction (XRPD) pattern of the solid is shown in FIG. 1, and the XRPD diffraction peak data thereof is shown in Table 1 below. The TGA/DSC spectrum is shown in FIG. 2. The TGA results show that the solid has a weight loss of 0.8% when heated to 150° C.; the DSC results show that the solid has an endothermic peak at 101.4° C. (onset temperature). The DVS spectrum is shown in FIG. 3, which shows that the vapor sorption of the solid at 25° C./80% RH is 0.17%, indicating that the sample has almost no hygroscopicity. The XRPD comparison pattern before and after the DVS test is shown in FIG. 4, which shows that the crystal form of the solid is unchanged before and after the DVS test. The PLM results are shown in FIG. 5, which indicate that the solid is irregular crystal particles. This crystal form is defined as crystal form A.

TABLE 1

XRPD diffraction peak data of crystal form A

| Peak No. | Position [°2θ] | Peak height [cts] | Left half peak width [°2θ] | d value [Å] | Relative peak intensity [%] |
|---|---|---|---|---|---|
| 1 | 4.16 | 798.23 | 0.1535 | 21.24 | 9.55 |
| 2 | 5.74 | 8358.08 | 0.1023 | 15.39 | 100.00 |
| 3 | 6.78 | 5563.58 | 0.1023 | 13.04 | 66.57 |
| 4 | 8.25 | 1533.96 | 0.1023 | 10.72 | 18.35 |
| 5 | 9.90 | 844.89 | 0.1023 | 8.93 | 10.11 |
| 6 | 10.86 | 5301.66 | 0.1023 | 8.15 | 63.43 |
| 7 | 11.44 | 413.51 | 0.1279 | 7.74 | 4.95 |
| 8 | 11.72 | 553.44 | 0.1023 | 7.55 | 6.62 |
| 9 | 12.36 | 700.77 | 0.1023 | 7.16 | 8.38 |
| 10 | 13.54 | 4194.13 | 0.1023 | 6.54 | 50.18 |
| 11 | 14.92 | 1476.66 | 0.1023 | 5.94 | 17.67 |
| 12 | 15.55 | 441.59 | 0.1023 | 5.70 | 5.28 |
| 13 | 16.70 | 4026.70 | 0.1279 | 5.31 | 48.18 |
| 14 | 17.23 | 2451.57 | 0.1279 | 5.15 | 29.33 |
| 15 | 17.53 | 1219.96 | 0.1023 | 5.06 | 14.60 |
| 16 | 18.10 | 1516.63 | 0.1535 | 4.90 | 18.15 |
| 17 | 18.33 | 498.11 | 0.1023 | 4.84 | 5.96 |
| 18 | 19.13 | 793.71 | 0.1279 | 4.64 | 9.50 |
| 19 | 19.56 | 1994.63 | 0.1279 | 4.54 | 23.86 |
| 20 | 20.16 | 1237.58 | 0.1279 | 4.40 | 14.81 |
| 21 | 20.62 | 902.33 | 0.1535 | 4.31 | 10.80 |
| 22 | 20.92 | 624.15 | 0.1023 | 4.25 | 7.47 |
| 23 | 21.33 | 914.94 | 0.1023 | 4.17 | 10.95 |
| 24 | 21.61 | 565.13 | 0.1023 | 4.11 | 6.76 |
| 25 | 22.26 | 967.29 | 0.1279 | 3.99 | 11.57 |
| 26 | 22.65 | 3513.86 | 0.1279 | 3.93 | 42.04 |
| 27 | 22.98 | 1002.54 | 0.1023 | 3.87 | 11.99 |
| 28 | 23.27 | 806.07 | 0.1535 | 3.82 | 9.64 |
| 29 | 24.07 | 1365.91 | 0.1023 | 3.70 | 16.34 |
| 30 | 24.49 | 508.65 | 0.1023 | 3.64 | 6.09 |
| 31 | 24.82 | 426.55 | 0.1023 | 3.59 | 5.10 |
| 32 | 25.60 | 958.58 | 0.1023 | 3.48 | 11.47 |
| 33 | 25.81 | 909.01 | 0.1023 | 3.45 | 10.88 |
| 34 | 26.66 | 347.03 | 0.1023 | 3.34 | 4.15 |
| 35 | 27.22 | 1612.57 | 0.1791 | 3.28 | 19.29 |
| 36 | 28.49 | 306.64 | 0.1535 | 3.13 | 3.67 |
| 37 | 28.78 | 415.44 | 0.1279 | 3.10 | 4.97 |
| 38 | 29.90 | 234.86 | 0.1023 | 2.99 | 2.81 |
| 39 | 30.62 | 314.52 | 0.1279 | 2.92 | 3.76 |
| 40 | 31.36 | 97.40 | 0.1023 | 2.85 | 1.17 |
| 41 | 31.75 | 234.43 | 0.1279 | 2.82 | 2.80 |
| 42 | 32.70 | 206.52 | 0.1279 | 2.74 | 2.47 |
| 43 | 33.14 | 213.96 | 0.1535 | 2.70 | 2.56 |
| 44 | 33.34 | 233.55 | 0.1535 | 2.69 | 2.79 |
| 45 | 33.77 | 173.97 | 0.1279 | 2.65 | 2.08 |
| 46 | 34.20 | 198.29 | 0.1023 | 2.62 | 2.37 |
| 47 | 35.55 | 225.55 | 0.1023 | 2.53 | 2.70 |
| 48 | 36.18 | 143.45 | 0.1535 | 2.48 | 1.72 |
| 49 | 37.40 | 89.65 | 0.2558 | 2.40 | 1.07 |
| 50 | 38.08 | 44.49 | 0.1535 | 2.36 | 0.53 |
| 51 | 38.77 | 69.90 | 0.1791 | 2.32 | 0.84 |
| 52 | 39.36 | 90.44 | 0.1535 | 2.29 | 1.08 |

Example 3 Preparation Example 2 of Crystal Form A of ((5-nitroquinolin-8-yl)oxy)methyl-isobutyryl-L-prolinate An aliquot of about 30 mg of the solid prepared according to Example 2 was weighed and put into a glass vial, and 0.5 mL of the solvents listed in Table 2 below were added respectively. The resulting suspension was placed under magnetic stirring (~1000 rpm) at room temperature for 6 days, and then centrifuged at 10,000 rpm to obtain a solid. The XRPD testing identified it as the same as the crystal prepared in Example 2, both of which were crystal form A.

TABLE 2

| Test No. | Solvent (v/v) | Result |
|---|---|---|
| A1 | Isopropanol | Crystal form A |
| A2 | Isopropanol/$H_2O$ (98:2 by volume) | Crystal form A |
| A3 | Isopropanol/$H_2O$ (96:4 by volume) | Crystal form A |
| A4 | Isopropanol/$H_2O$ (92:8 by volume) | Crystal form A |
| A5 | Isopropanol/$H_2O$ (85:15 by volume) | Crystal form A |
| A6 | $H_2O$ | Crystal form A |
| A7 | Isopropyl acetate | Crystal form A |
| A8 | Methyl tert-butyl ether | Crystal form A |
| A9 | n-heptane | Crystal form A |
| A10 | Dimethyl sulfoxide/cyclopentyl methyl ether, 1:2 | Crystal form A |
| A11 | Tetrahydrofuran/n-heptane, 1:2 | Crystal form A |
| A12 | Methanol/$H_2O$, 1:4 | Crystal form A |
| A13 | Acetone/n-heptane, 1:4 | Crystal form A |

Example 4 Preparation Example 3 of Crystal Form A of ((5-nitroquinolin-8-yl)oxy)methyl-isobutyryl-L-prolinate An aliquot of about 30 mg of the solid prepared according to Example 2 was weighed and put into a glass vial, and 0.5 mL of the solvents listed in Table 3 below were added respectively. The resulting suspension was placed under magnetic stirring (~1000 rpm) at 50° C. for 3 days, and then centrifuged at 10,000 rpm to obtain a solid. The XRPD testing identified it as the same as the crystal obtained in Example 2, both of which were crystal form A.

TABLE 3

| Test No. | Solvent (v/v) | Result |
|---|---|---|
| A14 | Cyclopentyl methyl ether | Crystal form A |
| A15 | $H_2O$ | Crystal form A |
| A16 | Isopropyl acetate | Crystal form A |
| A17 | Isopropanol/$H_2O$, 1:2 | Crystal form A |
| A18 | Methyl isobutyl ketone/methyl tert-butyl ether, 1:2 | Crystal form A |
| A19 | Ethyl acetate/isopropanol, 1:2 | Crystal form A |
| A20 | Toluene/n-heptane, 1:2 | Crystal form A |
| A21 | Dimethyltetrahydrofuran/n-heptane, 1:2 | Crystal form A |
| A22 | Methyl ethyl ketone/isopropanol, 1:2 | Crystal form A |
| A23 | Acetonitrile/cyclopentyl methyl ether, 1:4 | Crystal form A |
| A24 | Anisole/isopropyl acetate, 1:4 | Crystal form A |
| A25 | 1,4-Dioxane/cyclopentyl methyl ether, 1:4 | Crystal form A |

Example 5 Preparation Example 4 of Crystal Form A of (5-nitroquinolin-8-yl)oxy)methyl-isobutyryl-L-prolinate An aliquot of about 30 mg of the solid prepared according to Example 2 was weighed and put into a glass vial, and 0.5 mL of the solvents listed in Table 4 below were added respectively. The resulting suspension was placed in a temperature cycle (50→5° C., 0.1° C./min, 5→50° C., 0.375° C./min, for three cycles) under stirring, and then centrifuged at 10,000 rpm to obtain a solid. The XRPD testing identified it as the same as the crystal obtained in Example 2, both of which were crystal form A.

TABLE 4

| Test No. | Solvent (v/v) | Result |
|---|---|---|
| A26 | Isopropanol | Crystal form A |
| A27 | Methyl isobutyl ketone | Crystal form A |
| A28 | Isopropyl acetate | Crystal form A |
| A29 | Methyl tert-butyl ether | Crystal form A |
| A30 | Cyclopentyl methyl ether | Crystal form A |
| A31 | n-heptane | Crystal form A |
| A32 | $H_2O$ | Crystal form A |
| A33 | Ethanol/cyclopentyl methyl ether, 1:2 | Crystal form A |
| A34 | Toluene/isopropyl acetate, 1:4 | Crystal form A |
| A35 | Methyl ethyl ketone/isopropyl acetate, 1:4 | Crystal form A |

Example 6 Preparation Example 5 of Crystal Form A of ((5-nitroquinolin-8-yl)oxy)methyl-isobutyryl-L-prolinate An aliquot of about 30 mg of the solid prepared according to Example 2 was weighed and put into a glass vial, and 0.5 mL of the solvents listed in Table 5 below were added respectively. After the solution was stirred at 50° C. for 2 hours and filtered (PTFE filter membrane with pore size of 0.45 μm; manufacturer: Titan Chemical; model: syringe filter hydrophobic polytetrafluoroethylene (PTFE) 0.45 μm 13 mm), the resulting filtrate was placed in a biochemical incubator (manufacturer: Shanghai Yiheng Scientific Instrument Co., Ltd.; model: BPC-70F) in which the temperature was lowered from 50° C. to 5° C. at a cooling rate of 0.1° C./min. If the solution was still clear, the clear sample was transferred to −20° C. and left to stand overnight to obtain a solid, which was removed with a spatula. The XRPD testing identified it as the same as the crystal obtained in Example 2, both of which were crystal form A.

TABLE 5

| Test No. | Solvent (v/v) | Result |
|---|---|---|
| A36 | Isopropanol/$H_2O$, 9:1 | Crystal form A |
| A37 | Methyl isobutyl ketone/n-heptane, 1:1 | Crystal form A |
| A38 | Isopropyl acetate | Crystal form A |
| A39 | Methyl tert-butyl ether | Crystal form A |
| A40 | Cyclopentyl methyl ether | Crystal form A |

Example 7 Preparation Example 6 of Crystal Form A of ((5-nitroquinolin-8-yl)oxy)methyl-isobutyryl-L-prolinate An aliquot of about 30 mg of the solid prepared according to Example 2 was weighed and put into a glass vial, 1.0 mL of the positive solvents listed in Table 6 below were added respectively, and the solution was filtered. The anti-solvents listed in Table 6 below were added dropwise under stirring to the clear solution at room temperature until precipitation of solid. If there was no solid precipitation after adding about 9 mL of the anti-solvent, the dropwise addition was stopped, and the solution was centrifuged at 10,000 rpm to obtain a solid. The XRPD testing identified it as the same as the crystal obtained in Example 2, both of which were crystal form A.

TABLE 6

| Test No. | Positive solvent | Anti-solvent | Result |
|---|---|---|---|
| A41 | Methanol | Methyl tert-butyl ether | Crystal form A |
| A42 | Acetone | $H_2O$ | Crystal form A |

TABLE 6-continued

| Test No. | Positive solvent | Anti-solvent | Result |
|---|---|---|---|
| A43 | | n-heptane | Crystal form A |
| A44 | Acetonitrile | $H_2O$ | Crystal form A |
| A45 | Ethanol | n-heptane | Crystal form A |
| A46 | Tetrahydrofuran | n-heptane | Crystal form A |
| A47 | Dichloromethane | n-heptane | Crystal form A |

Example 8 Preparation Example 7 of Crystal Form A of ((5-nitroquinolin-8-yl)oxy)methyl-isobutyryl-L-prolinate An aliquot of about 30 mg of the solid prepared according to Example 2 was weighed and put into a 3 mL glass vial, and about 4 mL of the solvents listed in Table 7 below were added in another 20 mL glass vial. The open 3 mL glass vial was placed in the 20 mL glass vial, and then the 20 mL glass vial was sealed. The 20 mL glass vial was left to stand at room temperature until the solid surface became wet, or after being left to stand for 7 days, and then the XRPD testing was carried out. The XRPD testing identified it as the same as the crystal obtained in Example 2, both of which were crystal form A.

TABLE 7

| Test No. | Solvent | Result |
|---|---|---|
| A48 | Methyl isobutyl ketone | Crystal form A |
| A49 | Dimethyl sulfoxide | Crystal form A |
| A50 | $H_2O$ | Crystal form A |
| A51 | Ethanol | Crystal form A |
| A52 | Tetrahydrofuran | Crystal form A |
| A53 | Methyl tert-butyl ether | Crystal form A |
| A55 | Toluene | Crystal form A |
| A56 | Acetone | Crystal form A |
| A57 | Ethyl acetate | Crystal form A |
| A58 | 1,4-Dioxane | Crystal form A |
| A59 | Isopropanol | Crystal form A |
| A60 | Anisole | Crystal form A |

Example 9 Preparation Example 8 of Crystal Form A of ((5-nitroquinolin-8-yl)oxy)methyl-isobutyryl-L-prolinate An aliquot of about 30 mg of the solid prepared according to Example 2 was weighed and dissolved in 0.5-1.0 mL of the positive solvents listed in Table 8 below, and the solution was filtered. The resulting filtrate was transferred to a 3 mL glass vial, and about 4 mL of the anti-solvents listed in Table 8 below were added to another 20 mL glass vial. The open 3 mL glass vial with the filtrate was placed in the 20 mL glass vial, and then the 20 mL glass vial was sealed and left to stand at room temperature. When solid precipitation was observed, the solid was collected, and the XRPD testing was carried out. The XRPD testing identified it as the same as the crystal obtained in Example 2, both of which were crystal form A.

TABLE 8

| Test No. | Positive solvent (v/v) | Anti-solvent | Result |
|---|---|---|---|
| A61 | Methyl isobutyl | n-heptane | Crystal form A |
| A62 | ketone | Methyl tert-butyl ether | Crystal form A |

TABLE 8-continued

| Test No. | Positive solvent (v/v) | Anti-solvent | Result |
|---|---|---|---|
| A63 | | Isopropanol | Crystal form A |
| A65 | 1,4-Dioxane | Methyl tert-butyl ether | Crystal form A |
| A66 | Ethanol | $H_2O$ | Crystal form A |

Example 10 Preparation Example 9 of Crystal Form A of ((5-nitroquinolin-8-yl)oxy)methyl-isobutyryl-L-prolinate An aliquot of about 30 mg of the solid prepared according to Example 2 was weighed and put into a 3 mL glass vial, and 1.0-2.0 mL of the solvents listed in Table 9 below were added respectively. After the solution was shaken and filtered (PTFE filter membrane with pore size of 0.45 μm; manufacturer: Titan Chemical; model: syringe filter hydrophobic polytetrafluoroethylene (PTFE) 0.45 μm 13 mm), the filtrate was collected. The glass vial with the clear solution was sealed with parafilm, on which several small holes was poked, and the glass vial was left to stand at room temperature for slow evaporation. When there was solid precipitation, the resulting solid was collected, and the XRPD testing was carried out. The XRPD testing identified it as the same as the crystal obtained in Example 2, both of which were crystal form A.

TABLE 9

| Test No. | Solvent (v/v) | Result |
|---|---|---|
| A67 | Isopropanol | Crystal form A |
| A68 | Methyl isobutyl ketone | Crystal form A |
| A69 | Methyl ethyl ketone | Crystal form A |
| A70 | Dichloromethane | Crystal form A |
| A71 | 1,4-Dioxane | Crystal form A |

Example 11 Preparation of Crystal Form B of ((5-nitroquinolin-8-yl)oxy)methyl-isobutyryl-L-prolinate 30.5 mg of the solid prepared in Example 2 was dissolved in 1 mL of ethyl acetate. After filtration, n-heptane was slowly added, and a solid was precipitated when 7 mL was added. The solid was obtained by filtration and dried.

Figure 6:
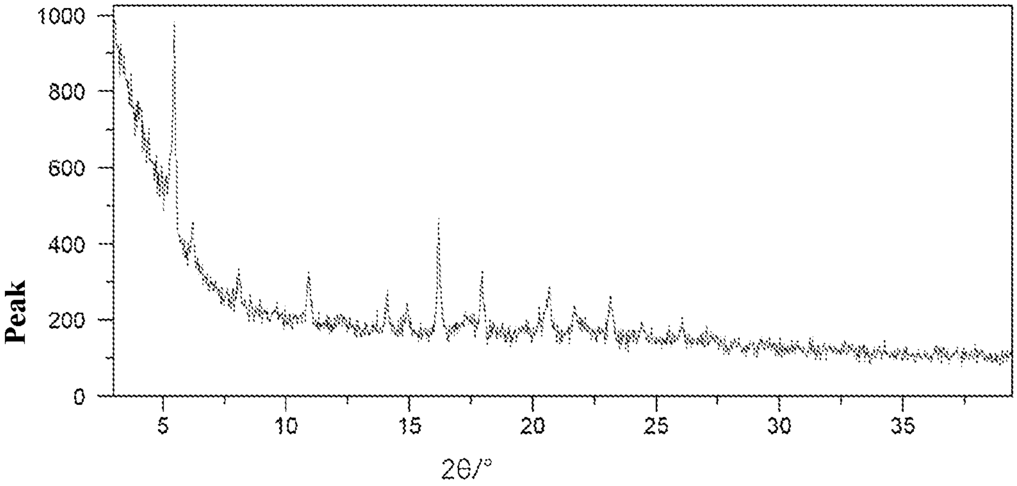
FIG. 6 is a XRPD pattern of crystal form B prepared in Example 11.
Figure 7:
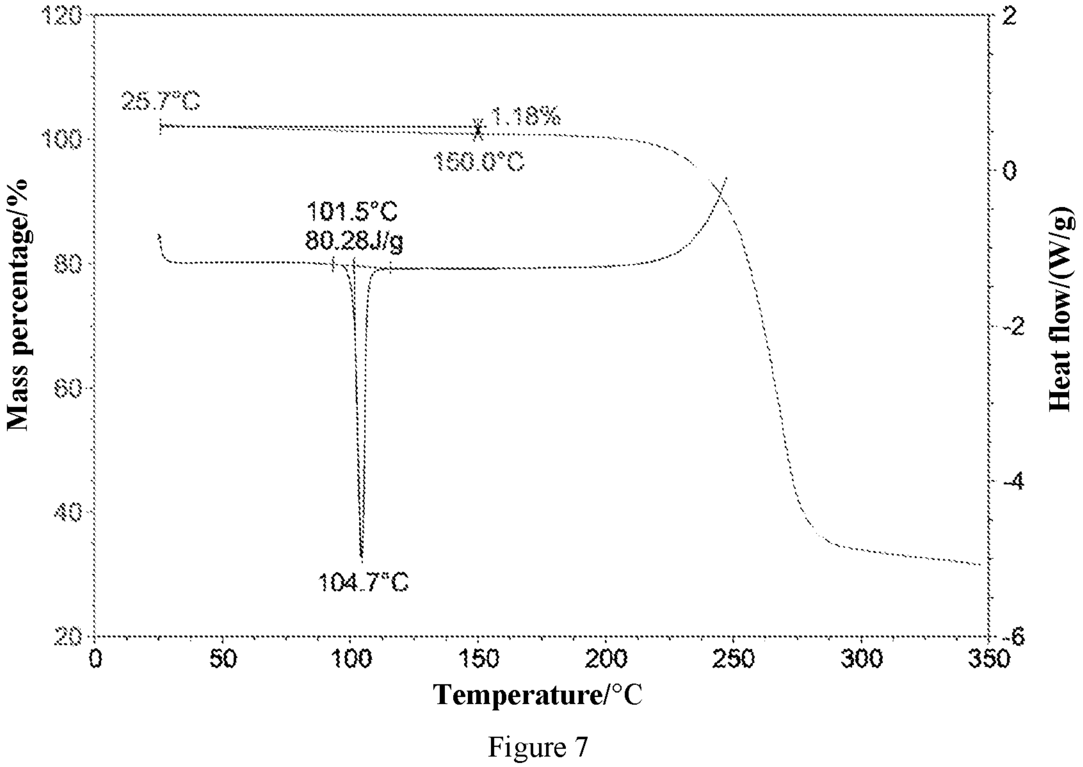
FIG. 7 is a TGA/DSC spectrum of crystal form B prepared in Example 11.
Figure 8:
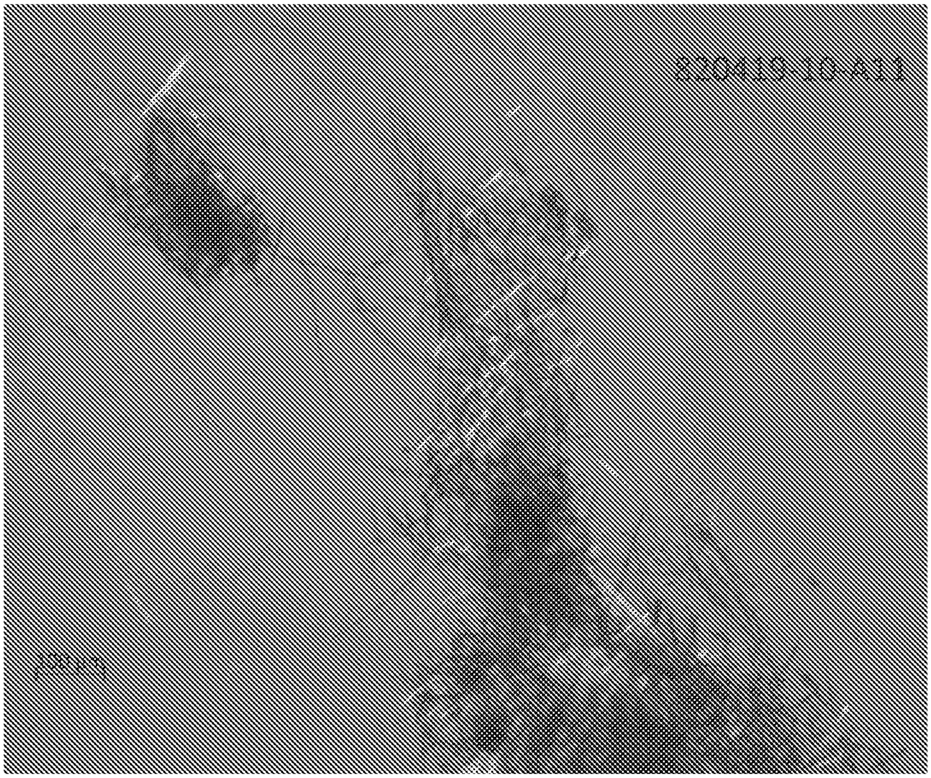
FIG. 8 is a PLM photograph of crystal form B prepared in Example 11.

The X-ray powder diffraction (XRPD) pattern of the solid is shown in FIG. 6, and the XRPD diffraction peak data are shown in Table 10 below. The TGA/DSC spectrum is shown in FIG. 7, showing that the solid has a weight loss of 1.2% when heated to 150° C. and has an endothermic peak at 101.5° C. (onset temperature). The PLM results show that the sample is needle-like with a length of about 100 μm (see FIG. 8).

This crystal form is defined as crystal form B.

TABLE 10

| XRPD diffraction peak data of crystal form B | | | | | |
|---|---|---|---|---|---|
| Peak No. | Position [°2θ] | Peak height [cts] | Left half peak width [°2θ] | d value [Å] | Relative peak intensity [%] |
| 1 | 5.44 | 455.57 | 0.1023 | 16.24 | 100.00 |
| 2 | 6.19 | 81.26 | 0.1023 | 14.28 | 17.84 |
| 3 | 8.06 | 63.18 | 0.1535 | 10.97 | 13.87 |
| 4 | 10.90 | 113.78 | 0.1023 | 8.12 | 24.98 |
| 5 | 12.18 | 23.30 | 0.6140 | 7.27 | 5.11 |

TABLE 10-continued

| XRPD diffraction peak data of crystal form B | | | | | |
|---|---|---|---|---|---|
| Peak No. | Position [°2θ] | Peak height [cts] | Left half peak width [°2θ] | d value [Å] | Relative peak intensity [%] |
| 6 | 14.09 | 106.71 | 0.1023 | 6.29 | 23.42 |
| 7 | 14.88 | 72.15 | 0.1535 | 5.95 | 15.84 |
| 8 | 16.17 | 268.11 | 0.1535 | 5.48 | 58.85 |
| 9 | 17.92 | 156.25 | 0.1279 | 4.95 | 34.30 |
| 10 | 20.66 | 127.28 | 0.1279 | 4.30 | 27.94 |
| 11 | 21.69 | 79.13 | 0.2047 | 4.10 | 17.37 |
| 12 | 23.13 | 119.03 | 0.1535 | 3.85 | 26.13 |
| 13 | 24.42 | 45.35 | 0.2047 | 3.64 | 9.95 |
| 14 | 26.03 | 56.77 | 0.1535 | 3.42 | 12.46 |

Test Example 1: Determination of the Water Solubility of the Compound ((5-nitroquinolin-8-yl)oxy)methyl-isobutyryl-L-prolinate Obtained in Example 1

The compound obtained in Example 1 can slowly release the active ingredient nitroxoline after entering the human body, and the latter can simultaneously inhibit the methionine aminopeptidase MetAP2 and the silent mating-type information regulation 2 homolog in vascular endothelial cells, exerting a synergistic inhibitory effect on tumor angiogenesis. Meanwhile, nitroxoline also has an inhibitory effect on the proliferation of tumor cells. In addition, the released active ingredient nitroxoline exerts a bacteriostatic effect by inhibiting the methionine aminopeptidase MetAP in bacteria.

The inventor first conducted a research on the water solubility of nitroxoline and the compound obtained in Example 1.

Experimental instruments: 96-well filter plate (MSHVN4510 or MSHVN4550, Millipore); electronic digital vortex (MS3 Digital, IKA); circulating water-type multipurpose vacuum pump (SHB-III, Zhengzhou Greatwall Science, Industry and Trade Co., Ltd.); balance (XSLT05, METTLER TOLEDO); ThermoMixer comfort (Eppendorf AG 22331 Hamburg); liquid chromatography (LC-30AD, Shimadzu); mass spectrometer (API4000, Applied); sampler (CTC Analytics AG System). Nitroxoline was synthesized by Wisdom Pharmaceutical Co., Ltd. according to the method disclosed in Journal of Heterocyclic Chemistry, 1971, vol. 8, p821.

Experimental procedures: 500 μL of phosphate buffer (pH=1.2, 4.5, 6.8 or 7.4) was added into a glass vial, 2 mg of compound powder was added. The vial was sealed with a cap and placed on a vortex (VORTEX-GENIE2) to mix well at room temperature for 24 hours. The solution was then subjected to vacuum filtration, the filtrate was processed, and the concentration of the compound was determined by LC/MS/MS.

The solubility results of the compound obtained in Example 1 are shown in Table 11 below.

TABLE 11

| Solubility of the compound obtained in Example 1 | | |
|---|---|---|
| Compound No. | Buffer pH | Solubility (μg/mL) |
| Nitroxoline | 7.4 | 351.73 |
| Compound obtained in Example 1 | 1.2 | 1012.57 |
| Compound obtained in Example 1 | 4.5 | 1045.45 |
| Compound obtained in Example 1 | 6.8 | 962.10 |
| Compound obtained in Example 1 | 7.4 | 978.26 |

Conclusion: Compared with nitroxoline (5-nitro-8-hydroxyquinoline), the water solubility of the compound obtained in Example 1 is several times higher in the buffer solution with pH 7.4, and its water solubility varies little at different pH, which can be regarded as basically unchanged. This feature is notably important in the development of drug formulations.

Test Example 2: Determination of the Stability of the Compound Obtained in Example 1 in Liver of Microsome and Plasma It is expected that the compound obtained in Example 1 is decomposed into nitroxoline in vivo, thereby exerting an anticancer effect. Liver microsomal enzymes and plasma metabolizing enzymes are important ways of compound metabolism in vivo. Thus, in vitro experiments were carried out to determine the stability of the compound obtained in Example 1 in liver microsome and plasma.

1. Determination of the Stability in Liver Microsome

Experimental instruments: thermostatic oscillator (SHA-B, Guohua Instrument); centrifuge (5810R, Eppendorf), mass spectrometer (API4000, Applied), liquid chromatography (LC-30AD, Shimadzu); sampler (CTC Analytics AG System, CTC).

Experimental procedures: to 100 mM phosphate buffer was added 25 μg/mL alamethicin (Aldrich Reagents), 5 mM magnesium chloride and 0.5 mg/mL microsomes (XENOTECH) to prepare a reaction solution without coenzymes. To a portion of the reaction solution was added 1 mM reduced nicotinamide adenine dinucleotide phosphate (Aldrich Reagents) and 5 mM uridine diphosphate glucuronic acid (Aldrich Reagents) to prepare a reaction solution with coenzymes. Then, to the two reaction solutions was added the working solution of the compound obtained in Example 1, so that the final concentration of the compound was 2 μM. Immediately after mixing well, 50 μL of the solution was collected as the 0-minute sample, and another 50 μL was collected after 30 minutes of incubation of the remaining sample at 37° C. The proteins in all collected samples were immediately precipitated, and the supernatants were collected by centrifugation, in which the compound concentrations were determined by LC/MS/MS.

The stability results of the compound obtained in Example 1 in microsome are shown in Table 12 below.

TABLE 12

Stability of the compound obtained in Example 1 in microsome

| Compound No. | Percentage (%) of remaining compound in human liver microsomes | | Percentage (%) of remaining compound in dog liver microsomes | | Percentage (%) of remaining compound in rat liver microsomes | | Percentage (%) of remaining compound in mouse liver microsomes | |
|---|---|---|---|---|---|---|---|---|
| | With coenzyme | Without coenzyme | With coenzyme | Without coenzyme | With coenzyme | Without coenzyme | With coenzyme | Without coenzyme |
| Compound obtained in Example 1 | 26.92 | 59.42 | 33.13 | 53.50 | 3.64 | 46.82 | 0.09 | 49.07 |

Conclusion: The above data can show that the compound obtained in Example 1 can be rapidly converted into nitroxoline after entering the body, which reduces the possibility of unnecessary biological toxicity, and the compound has the advantages and characteristics for drug development.

Test Example 3: Pharmacokinetic Assay of the Compound Obtained in Example 1 in Rats In this experiment, after a single intravenous or oral administration of nitroxoline and the compound obtained in Example 1 to rats, the changes in the concentration of the compound nitroxoline in rat plasma were studied, so as to evaluate the in vivo pharmacokinetic behaviors of nitroxoline and the compound obtained in Example 1 in rats.

1. Experimental Instruments

Tandem quadrupole mass spectrometer (API4000, Applied Biosystems, USA), liquid chromatography (1200, Agilent), autosampler (CTC Analytics HTC PAL), Analyst v1.6.2 by Applied Biosystems, USA, refrigerated centrifuge (1-15PK, Sigma), vortex (VX-III, Beijing Targin Technology Co., Ltd).

2. Pharmacokinetic Experiments

Male SD rats (Beijing Vital River Laboratory Animal Technology Co., Ltd., laboratory animal production license No.: SCXK (Beijing) 2016-0006, laboratory animal certificate No.: 11400700325643), 3 rats per group, weight 180-250 g, 6-7 weeks old, were fasted overnight before drug administration with free access to water, and food was given 4 hours after drug administration. The compound to be tested was put into an EP tube, 1.017 mL dimethyl sulfoxide, 2.035 mL Solutol® and sterile water for injection (the volume ratio of the three was 1:2:17, v:v:v) were added, and the EP tube was sonicated for 20 minutes to fully dissolve the compound (formulation concentration of the compound: 0.005 mmol/mL). The intravenous dose was 0.01 mmol/kg, and the oral dose was 0.1 mmol/kg. 0.3 ml of whole blood was collected from the orbital venous plexus before drug administration (0 hour) and 0.0833, 0.25, 0.5, 1, 2, 4, 6, 8, 10, 24, 28, 32, and 48 hours after drug administration (the sampling points were adjusted according to the situation) and placed in a centrifuge tube containing EDTA-K2 (Aldrich Reagents) for anticoagulation, which was placed in crushed ice after sample collection. The tube was centrifuged at 5000 rpm for 5 minutes within 0.5 hours of sample collection. All clean plasma were isolated and placed in another clean centrifuge tube, the stabilizing solution was added at a ratio of 100:3 (plasma/stabilizing solution, v/v), and the tube was placed in a −20° C. refrigerator until testing.

23

The preparation method of the stabilizing solution: 200 mg of vitamin C (Aldrich Reagents) was dissolved in 8 mL of physiological saline, and then 2 mL of formic acid was added and mixed well.

3. Determination of Sample Concentration

Standard curve: A series of working solutions for standard curve was prepared, 5 μL of which was added to 50 μL blank rat plasma. 150 μL of internal standard working solution (a solution of 2 ng/mL diphenhydramine (Aldrich Reagents) in acetonitrile) was added, and the resulting solution was vortexed for 1 minute. After centrifuging at 4° C., 12,000 rpm for 10 minutes, 100 μL of the supernatant was collected into a sample tube, and 10 μL was injected into the LC/MS system for determination.

Sample to be tested: to 50 μL of plasma sample to be tested was added 5 μL of diluted working solution, then 150 μL of internal standard working solution (a solution of 2 ng/mL diphenhydramine in acetonitrile), and the resulting solution was vortexed for 1 minute. After centrifuging at 4° C., 12,000 rpm for 10 minutes, 100 μL of the supernatant was collected into a sample tube, and 10 μL was injected into the LC/MS system for determination. Pharmacokinetic parameters were calculated using WinNonlin V6.2 non-compartmental model.

The testing results are shown in Table 13 to Table 14 below.

TABLE 13

Plasma concentration of nitroxoline after oral administration of nitroxoline to SD rats

| Time (hours) | Rat-04 | Rat-05 | Rat-06 | Mean | Standard deviation |
|---|---|---|---|---|---|
| 0.00 | <5.0 | <5.0 | <5.0 | Not applicable (N/A) | N/A |
| 0.08 | 13864 | 9616 | 9797 | 11092 | 2402 |
| 0.25 | 9102 | 3736 | 5661 | 6167 | 2718 |
| 0.50 | 2214 | 1248 | 2410 | 1957 | 622 |
| 1.0 | 1146 | 639 | 766 | 850 | 263 |
| 2.0 | 278 | 334 | 406 | 339 | 63.8 |
| 4.0 | 161 | 168 | 54.4 | 128 | 63.5 |
| 6.0 | 12.2 | 54.2 | 16.9 | 27.7 | 23.0 |
| 8.0 | 8.37 | 36.7 | 5.77 | 16.9 | 17.1 |
| 10 | 8.82 | 14.6 | <5.0 | 11.7 | N/A |
| 24 | <5.0 | 14.6 | <5.0 | N/A | N/A |
| Half-life (h) | | | 1.39 | | |

TABLE 14

Plasma concentration of nitroxoline after oral administration of the compound obtained in Example 1 to SD rats Plasma concentration of nitroxoline (ng/mL)

| Time (hours) | Rat-39 | Rat-40 | Rat-41 | Mean | Standard deviation |
|---|---|---|---|---|---|
| 0 | <5.0 | <5.0 | <5.0 | N/A | N/A |
| 0.083 | 1210 | 545 | 846 | 867 | 333 |
| 0.25 | 9380 | 1300 | 4470 | 5050 | 4071 |
| 0.5 | 8240 | 1330 | 1640 | 3740 | 3903 |
| 1 | 2540 | 798 | 490 | 1280 | 1105 |
| 2 | 1670 | 1020 | 329 | 1010 | 671 |
| 4 | 958 | 274 | 174 | 469 | 427 |
| 6 | 349 | 4.53 | 30.6 | 128 | 192 |

24

TABLE 14-continued

Plasma concentration of nitroxoline after oral administration of the compound obtained in Example 1 to SD rats Plasma concentration of nitroxoline (ng/mL)

| Time (hours) | Rat-39 | Rat-40 | Rat-41 | Mean | Standard deviation |
|---|---|---|---|---|---|
| 8 | 518 | <5.0 | 20.6 | 269 | N/A |
| 10 | 319 | <5.0 | 26.6 | 173 | N/A |
| 12 | 93.2 | <5.0 | 17.6 | 55.4 | N/A |
| Half-life (h) | | 1.68 | | | |

Conclusion: Compared with nitroxoline, the compound obtained in Example 1 has significantly improved absorption or half-life in rats. As a result, the drug molecule has a good compliance improvement in reducing the dosage or the frequency of administration.

Test Example 4: Pharmacokinetic Assay of the Compound Obtained in Example 1 in Dogs Nitroxoline is mainly metabolized by Phase II metabolism in the liver with a high metabolism rate, thus the in vivo half-life is short. In this experiment, after a single intravenous or oral administration of nitroxoline and the compound obtained in Example 1 to dogs, the changes in the concentration of the compound nitroxoline in dog plasma were studied, so as to evaluate the in vivo pharmacokinetic behaviors of nitroxoline and the compound obtained in Example 1.

1. Experimental Instruments

Tandem quadrupole mass spectrometer (API5500, Applied Biosystems, USA), liquid chromatography (1200, Agilent), autosampler (CTC Analytics HTC PAL), Analyst v1.6.2 by Applied Biosystems, USA.

2. Pharmacokinetic Experiments

Male beagles (Beijing Marshall Bioresources Co., Ltd., laboratory animal production license No.: SCXK (Beijing) 2016-0001, laboratory animal certificate No.: 11400600001728), 3 beagles per group, weight 10-13 kg, 20-22 months old, were fasted overnight before drug administration with free access to water, and food was given 4 hours after drug administration. The compound to be tested was put into an EP tube, dimethyl sulfoxide, Solutol® and sterile water for injection (the volume ratio of the three was 1:2:17, v:v:v) were added, and the EP tube was sonicated for 20 minutes to fully dissolve the compound (formulation concentration of the compound: 0.005 mmol/mL). The intravenous dose was 0.01 mmol/kg, and the oral dose was 0.1 mmol/kg. 0.3 ml of whole blood was collected from the jugular vein before drug administration (0 hour) and 0.0833, 0.25, 0.5, 0.75, 1, 2, 4, 6, 8, 10 and 12 hours after drug administration (the sampling points were adjusted according to the situation) and placed in a centrifuge tube containing EDTA-K2 (Aldrich Reagents) for anticoagulation, which was placed in crushed ice after sample collection. The tube was centrifuged at 1530 g for 10 minutes within 0.5 hours of sample collection. All clean plasma were isolated and placed in another clean centrifuge tube, which was placed in a −20° C. refrigerator until testing.

3. Determination of Sample Concentration

A series of solutions for standard curve was prepared. To 10 μL of solutions for standard curve and samples was added 1000 μL of internal standard working solution (a solution of 5 ng/mL verapamil (Aldrich Reagents), 50 ng/mL glibenclamide (Aldrich Reagents) and 50 ng/mL diclofenac (Aldrich Reagents) in acetonitrile) was added, and the resulting solution was vortexed for 5 minutes. After centrifuging at 4° C., 3700 rpm for 10 minutes, 60 μL of the supernatant was collected into a sample tube and mixed well with 120 μL of water, and 10 μL of the mixed solution was injected into the LC/MS system for determination. Pharmacokinetic parameters were calculated using WinNonlin V6.2 non-compartmental model.

The testing results are shown in Table 15 to Table 18 below.

TABLE 15

Plasma concentration of nitroxoline after intravenous injection of nitroxoline to beagles

| Time (hours) | Plasma concentration of nitroxoline (ng/mL) Dog-01 | Dog-02 | Dog-03 | Mean | Standard deviation |
|---|---|---|---|---|---|
| 0 | <5.0 | <5.0 | <5.0 | N/A | N/A |
| 0.083 | 8360 | 11500 | 10400 | 10100 | 1590 |
| 0.25 | 4420 | 5140 | 3320 | 4290 | 917 |
| 0.5 | 1220 | 1250 | 670 | 1050 | 327 |
| 0.75 | 406 | 393 | 299 | 366 | 58.4 |
| 1 | 187 | 164 | 178 | 176 | 11.6 |
| 2 | 37.1 | 34.8 | 20.1 | 30.7 | 9.22 |
| 4 | <5.0 | <5.0 | <5.0 | <5.0 | N/A |
| 6 | <5.0 | <5.0 | <5.0 | <5.0 | N/A |
| 8 | <5.0 | <5.0 | <5.0 | <5.0 | N/A |
| 10 | <5.0 | <5.0 | <5.0 | <5.0 | N/A |
| 12 | <5.0 | <5.0 | <5.0 | <5.0 | N/A |
| Half-life (h) | | | 0.36 | | |
| $AUC_{0\text{-}inf}$ ($ng*hmL^{-1}$) | | 3300 | | | |

TABLE 16

Plasma concentration of nitroxoline after oral administration of nitroxoline to beagles

| Time (hours) | Plasma concentration of nitroxoline (ng/mL) Dog-04 | Dog-05 | Dog-06 | Mean | Standard deviation |
|---|---|---|---|---|---|
| 0 | <5.0 | <5.0 | <5.0 | N/A | N/A |
| 0.083 | 4710 | 4930 | 914 | 3520 | 2258 |
| 0.25 | 6590 | 5960 | 4320 | 5620 | 1172 |
| 0.5 | 3990 | 3260 | 3300 | 3520 | 410 |
| 0.75 | 1860 | 2370 | 2250 | 2160 | 267 |
| 1 | 1030 | 1490 | 1360 | 1290 | 237 |
| 2 | 120 | 257 | 457 | 278 | 169 |
| 4 | 72.3 | 49.4 | 71.6 | 64.4 | 13.0 |
| 6 | 58.9 | 54.6 | 42.1 | 51.9 | 8.73 |
| 8 | 45.2 | 34.9 | 30.9 | 37.0 | 7.38 |
| 10 | 29.2 | 32.2 | <5.0 | 30.7 | N/A |
| 12 | <5.0 | 22.3 | 35.6 | 29.0 | N/A |
| Half-life (h) | | | 3.62 | | |
| $AUC_{0\text{-}inf}$ ($ng*hmL^{-1}$) | | 4780 | | | |

TABLE 17

Plasma concentration of nitroxoline after intravenous injection of the compound obtained in Example 1 to beagles

| Time (hours) | Plasma concentration of nitroxoline (ng/mL) Dog-10 | Dog-11 | Dog-12 | Mean | Standard deviation |
|---|---|---|---|---|---|
| 0 | <5.0 | <5.0 | <5.0 | N/A | N/A |
| 0.083 | 6280 | 4660 | 5630 | 5520 | 815 |
| 0.25 | 2170 | 1130 | 1620 | 1640 | 520 |
| 0.5 | 593 | 232 | 391 | 405 | 181 |
| 0.75 | 185 | 75.6 | 151 | 137 | 56.0 |
| 1 | 88.2 | 37.5 | 76.7 | 67.5 | 26.6 |
| 2 | 16.9 | 16.7 | 22.5 | 18.7 | 3.29 |
| 4 | 6.30 | 5.21 | 12.5 | 8.00 | 3.93 |
| 6 | 7.52 | 3.93 | 12.2 | 7.88 | 4.15 |
| 8 | 3.59 | <5.0 | 7.71 | 5.65 | N/A |
| 10 | <5.0 | <5.0 | <5.0 | <5.0 | N/A |
| 12 | <5.0 | <5.0 | <5.0 | <5.0 | N/A |
| Half-life (h) | | | 2.42 | | |
| $AUC_{0\text{-}inf}$ ($ng*hmL^{-1}$) | | 1290 | | | |

TABLE 18

Plasma concentration of nitroxoline after oral administration of the compound obtained in Example 1 to beagles

| Time (hours) | Plasma concentration of nitroxoline (ng/mL) Dog-13 | Dog-14 | Dog-15 | Mean | Standard deviation |
|---|---|---|---|---|---|
| 0 | <5.0 | <5.0 | <5.0 | N/A | N/A |
| 0.083 | 13000 | 2940 | 13000 | 9650 | 5808 |
| 0.25 | 10000 | 6580 | 8580 | 8390 | 1718 |
| 0.5 | 3500 | 4220 | 8900 | 5540 | 2932 |
| 0.75 | 1430 | 2190 | 7610 | 3740 | 3370 |
| 1 | 795 | 895 | 4770 | 2150 | 2267 |
| 2 | 123 | 76.5 | 224 | 141 | 75.4 |
| 4 | 33.9 | 26.3 | 179 | 79.7 | 86.1 |
| 6 | 31.1 | 30.4 | 100 | 53.8 | 40.0 |
| 8 | 20.1 | 22.6 | 67.4 | 36.7 | 26.6 |
| 10 | 18.4 | 34.8 | 23.7 | 25.6 | 8.37 |
| 12 | 9.60 | 27.1 | 11.8 | 16.2 | 9.53 |
| Half-life (h) | | | 3.07 | | |
| $AUC_{0\text{-}inf}$ ($ng*hmL^{-1}$) | | 8750 | | | |

Conclusion: It can be seen from the data that, compared with nitroxoline, the compound obtained in Example 1 has good absorption in beagle dogs, indicating that the administration dosage of the drug molecule can be effectively reduced by using the prodrug molecule.

Test Example 5 Stability Test of Crystal Form A of the Present Invention

The crystal forms obtained in Examples 2-10 were packaged in double-layer PE bags+aluminum foil bags+cardboard barrels, sealed and stored at a temperature of 40° C. and a relative humidity of 75%; a temperature of 25° C. and a relative humidity of 60%; at 5±3° C. for 6 months. The inspection items (appearance, moisture, related substance 1, related substance 2, content) were tested, and the specific test methods were as follows. The results are shown in Table 19. It can be seen from Table 19 that the impurity content of crystal form A is relatively low, and the impurity content does not substantially increase under each condition, indicating that crystal form A has good stability under long-term conditions.

1 Moisture 1.1. Instruments and Equipments

Moisture Meter

Electronic balance 1.2 Reagents

Karl Fischer titrant: analytical grad

Anhydrous methanol: analytical grade 1.3 Detection Method

About 50 mL of methanol was pumped into the titration beaker for pre-titration;

About 1.0 g of the test sample was accurately weighed and put into the titration beaker, stirred to dissolve, and the moisture of the test sample was titrated;

The weight of the test sample added, the concentration of the Karl Fischer titrant and the volume of the Karl Fischer titrant consumed during determination were recorded; the moisture of the second test sample was determined using the same method.

1.4 Calculation Formula $$\text{Moisture } (\%) = \frac{V \times F}{W \times 1000} \times 100\%$$

V—Volume of Karl Fischer titrant consumed for the test sample, mL;

F—Equivalent mass of water per 1 mL of Karl Fischer titrant, mg/mL;

W—Weighed sample amount of the test sample, g.

2 Related Substance 1

2.1 Chromatographic Conditions: High Performance Liquid Chromatography (HPLC)

Column: Waters XBridge C18 4.6×150 mm, 5 μm

Detector: UV or equivalent detector

Wavelength: 210 nm

Column temperature: 35° C.

Flow rate: 1.0 mL/min

Injection volume: 10 μL

Needle Wash: Acetonitrile

Mobile phase gradient:

| Time (min) | Mobile phase A: 0.1% aqueous phosphoric acid solution | Mobile Phase B: Acetonitrile |
|---|---|---|
| 0.0 | 90 | 10 |
| 10.0 | 55 | 45 |
| 15.0 | 40 | 60 |
| 20.0 | 5 | 95 |
| 21.0 | 90 | 10 |
| 30.0 | 90 | 10 |

2.2 Reagents and Reference Substances

Acetonitrile (chromatographic grade)

Phosphoric acid (chromatographic grade)

Dichloromethane (chromatographic grade)

Reference substance of 5-nitro-8-hydroxyquinoline: the same structural formula as 5-nitro-8-hydroxyquinoline Reference substance of ((5-nitroquinolin-8-yl)oxy) methyl-isobutyryl-L-prolinate: the same structural formula as ((5-nitroquinolin-8-yl)oxy)methyl-isobutyryl-L-prolinate Reference substance of impurity 1:

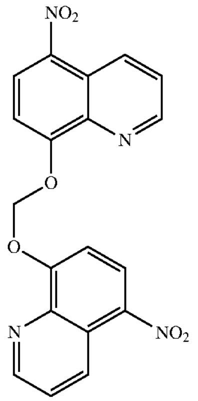 [SMILES: O=[N+]([O-])c1ccc(OCOc2ccc([N+](=O)[O-])c3cccnc23)c2ncccc12]

Reference substance of impurity 2:

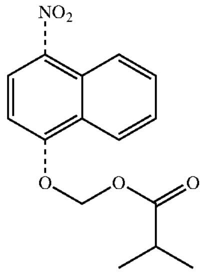

2.3 Solution Preparation

1) Mobile phase A: 0.1% aqueous phosphoric acid solution 1.0 mL of phosphoric acid were accurately measured and put into 1000 mL of ultrapure water and mixed well.

2) Mobile phase B: Acetonitrile

3) Diluent (blank solution): Acetonitrile

4) System suitability solution:

About 25 mg of reference substance of 5-nitro-8-hydroxyquinoline and about 25 mg of reference substance of impurity 2 were accurately weighed and put into a 50 mL volumetric flask. The diluent was added to dissolve the substances and dilute the solution to the mark. The solution was shaken well and labeled as Solution 1.

About 5 mg of reference substance of impurity 1 was weighed and put into a 50 mL volumetric flask. Dichloromethane that was already heated in a water bath at 40° C. was used to completely dissolve the substance and dilute the solution to the mark. The solution was shaken well and labeled as Solution 2.

About 50 mg of reference substance of ((5-nitroquinolin-8-yl)oxy)methyl-isobutyryl-L-prolinate was accurately weighed and put into a 100 mL volumetric flask. An appropriate amount of diluent was added to dissolve the substance, and then 1.0 mL of Solution 1 and 5.0 mL of Solution 2 were accurately added, and the diluent was added to dilute the solution to the mark. The solution was shaken well and labeled as the system suitability solution.

5) Sensitivity solution 1.0 mL of the system suitability solution was accurately measured and put into a 100 mL volumetric flask. The diluent was added to dilute the solution to the mark, and the solution was shaken well. 1.0 mL of the above solution was accurately measured and put into a 20 mL volumetric flask.

The diluent was added to dilute the solution to the mark, and the solution was shaken well.

6) Test sample solution

About 25 mg of the test sample was accurately weighed and put into a 50 mL volumetric flask. The diluent was added to dissolve the substance and dilute the solution to the mark, and the solution was shaken well.

2.4 Calculation: The Blank was Subtracted

1)

$$\text{Impurity (\%)} = \frac{A_U}{A_T} \times 100\%$$

$A_U$—the peak area of impurities in the test sample solution;

$A_T$—Total peak area of the test sample solution.

2) Total impurity (%)=Σ single impurity

| Name | Retention time (RT)/min | Relative retention time (RRT) |
|---|---|---|
| 5-Nitro-8-hydroxyquinoline | ~9.0 | 0.75 |
| ((5-Nitroquinolin-8-yl)oxy)methyl-isobutyryl-L-prolinate | ~11.9 | 1.00 |
| Impurity 1 | ~12.7 | 1.07 |
| Impurity 2 | ~13.6 | 1.15 |

3 Related Substance 2 (D-isobutyrylproline)

3.1 Chromatographic Conditions: High Performance Liquid Chromatography (HPLC)

Column: Synergi Hydro RP 4.6×250 mm, 4 μm

Detector: UV or equivalent detector

Wave length: 210 nm

Column temperature: 35° C.

Flow rate: 1.0 mL/min

Injection volume: 5 μL

Needle Wash: Acetonitrile

Mobile phase gradient:

| Time (min) | Mobile phase A: 0.1% aqueous phosphoric acid solution | Mobile Phase B: Acetonitrile |
|---|---|---|
| 0.0 | 75 | 25 |
| 8.0 | 65 | 35 |
| 10.0 | 20 | 80 |
| 10.1 | 75 | 25 |
| 20.0 | 75 | 25 |

3.2 Reagents and Reference Substances

Acetonitrile (chromatographic grade)

Phosphoric acid (chromatographic grade)

Ultrapure water

Reference substance of related substance 2: D-isobutyrylproline 3.3 Solution Preparation 1) Mobile phase A: 0.1% aqueous phosphoric acid solution 2) Mobile phase B: Acetonitrile 3) Diluent (blank solution): 50% aqueous acetonitrile solution 4) Reference substance solution About 40 mg of reference substance of related substance 2 was accurately weighed and put into a 100 mL volumetric flask. The diluent was added to dissolve the substance and dilute the solution to the mark, and the solution was shaken well. 1.0 mL of the above solution was accurately measured and put into a 100 mL volumetric flask. The diluent was added to dilute the solution to the mark, and the solution was shaken well. Two solutions were prepared in parallel and labeled as RS1/RS2 respectively.

5) Test sample solution

About 20 mg of the test sample was accurately weighed and put into a 10 mL volumetric flask. The diluent was added to dissolve the test sample and dilute the solution to the mark, and the solution was shaken well. Two solutions were prepared in parallel and labeled as S1/S2 respectively.

3.4 Calculation: Only the Peak of Related Substance 2 was Integrated $$\text{Recovery rate (\%)} = \frac{A_{RS2} \times M_{RS1}}{\overline{A_{RS1}} \times M_{RS2}} \times 100\%$$

$$\text{Content of related substance 2(\%)} = \frac{A_S \times M_{RS1} \times 10}{\overline{A_{RS1}} \times M_S \times 10000} \times P \times 100\%$$

$A_{RS2}$—Average peak area of reference solution 2;

$\overline{A_{RS1}}$—Average peak area of 5 injections of reference solution 1;

As—Peak area of related substance 2 in the test sample solution;

$M_{RS1}$—Weighed sample amount of related substance 2 in reference solution 1, mg;

Ms—Weighed sample amount of the test sample in the test sample solution, mg;

$M_{RS2}$—Weighed sample amount of related substance 2 in reference solution 2, mg;

| Name | Retention time (RT)/min |
|---|---|
| Related substance 2 | ~4.8 |

4 Content 4.1 Chromatographic Conditions: High Performance Liquid Chromatography (HPLC)

Column: Waters XBridge C18 4.6×150 mm, 5 μm

Detector: UV or equivalent detector

Wave length: 210 nm

Column temperature: 35° C.

Flow rate: 1.0 mL/min

Injection volume: 5 μL

Needle Wash: Acetonitrile

Mobile phase: 10 mM aqueous $KH_2PO_4$ solution (pH 2.8): ACN=57:43 (V/V)

Running time: 10 min 4.2 Reagents and Reference Substances

Potassium dihydrogen phosphate (chromatographic grade)

Acetonitrile (chromatographic grade)

Phosphoric acid (chromatographic grade)

Reference substance of ((5-nitroquinolin-8-yl)oxy)methyl-isobutyryl-L-prolinate: the same structural formula as ((5-nitroquinolin-8-yl)oxy)methyl-isobutyryl-L-prolinate 4.3 Solution Preparation 1) Mobile phase: 10 mM aqueous $KH_2PO_4$ solution (pH 2.8): ACN=57:43 (V/V)

1.36 g of $KH_2PO_4$ was weighed and put into 1000 mL of ultrapure water and dissolved completely. The pH was adjusted to 2.8 with phosphoric acid, and the solution was filtered with 0.45 μm filter membrane.

2) Diluent (blank solution): acetonitrile:ultrapure water=43:57 (v/v)

430 mL of acetonitrile and 570 mL of ultrapure water were measured, mixed well and sonicated.

3) Reference substance solution

About 20 mg of reference substance of ((5-nitroquinolin-8-yl)oxy)methyl-isobutyryl-L-prolinate was accurately weighed and put into a 100 mL volumetric flask. The diluent was added to dissolve the substance and dilute the solution to the mark, and the solution was shaken well. Two solutions were prepared in parallel.

4) Test sample solution

About 20 mg of the test sample was accurately weighed and put into a 100 mL volumetric flask. The diluent was added to dissolve the test sample and dilute the solution to the mark, and the solution was shaken well. Two solutions were prepared in parallel.

4.4 Calculation $$\text{Recovery rate (\%)} = \frac{A_{RS2} \times M_{RS1}}{\overline{A_{RS1}} \times M_{RS2}} \times 100\%$$

$$\text{Content (\%)} = \frac{A_S \times M_{RS1}}{\overline{A_{RS1}} \times M_S \times (1 - \text{Moisture \%})} \times P \times 100\%$$

$A_{RS2}$—Average peak area of reference solution 2;

$\overline{A_{RS1}}$—Average peak area of 5 injections of reference solution 1;

As—Peak area of ((5-nitroquinolin-8-yl)oxy)methyl-isobutyryl-L-prolinate in the test sample solution;

$M_{RS1}$—Weighed sample amount of reference substance of ((5-nitroquinolin-8-yl)oxy)methyl-isobutyryl-L-prolinate in reference solution 1, mg;

Ms—Weighed sample amount of the test sample in the test sample solution, mg;

$M_{RS2}$—Weighed sample amount of reference substance of ((5-nitroquinolin-8-yl)oxy)methyl-isobutyryl-L-prolinate in reference solution 2, mg;

P—Content of reference substance of ((5-nitroquinolin-8-yl)oxy)methyl-isobutyryl-L-prolinate, %.

| Name | Retention time (RT)/min |
|---|---|
| ((5-Nitroquinolin-8-yl)oxy)methyl-isobutyryl-L-prolinate | ~4.0 |

What is claimed is:

1. A crystal form of ((5-nitroquinolin-8-yl)oxy)methyl-isobutyryl-L-prolinate, characterized in that, the X-ray powder diffraction pattern thereof, which is obtained by using Cu-Kα irradiation and expressed in 2θ angle, comprises characteristic peaks at 5.74±0.2°, 6.78±0.2°, 10.86±0.2°, 13.54±0.2°, 16.70±0.2° and 22.65±0.2°.

2. The crystal form of ((5-nitroquinolin-8-yl)oxy)methyl-isobutyryl-L-prolinate according to claim 1, characterized in that, the X-ray powder diffraction pattern thereof, which is obtained by using Cu-Kα irradiation and expressed in 2θ angle, comprises characteristic peaks at 5.74±0.2°, 6.78±0.2°, 8.25±0.2°, 10.86±0.2°, 13.54±0.2°, 14.92±0.2°, 16.70±0.2°, 17.23±0.2°, 18.10±0.2°, 19.56±0.2°, 22.65±0.2° and 27.22±0.2°.

3. The crystal form of ((5-nitroquinolin-8-yl)oxy)methyl-isobutyryl-L-prolinate according to claim 1, characterized in that, the differential scanning calorimetry of the crystal form shows an endothermic peak at 101.4° C.

4. A method for preparing the crystal form of ((5-nitroquinolin-8-yl)oxy)methyl-isobutyryl-L-prolinate according to claim 1, characterized in that, the method comprises the following steps of:

mixing Solution I containing ((5-nitroquinolin-8-yl)oxy)methyl-isobutyryl-L-prolinate and a positive solvent with an anti-solvent to precipitate a solid, and performing solid-liquid separation to obtain the crystal form;

the positive solvent is-one or more solvents selected from the group consisting of ester solvent, $C_1$-$C_6$ alcohol solvent, ketone solvent, nitrile solvent, ether solvent and lower halogenated alkane solvent;

the anti-solvent is one or more solvents selected from the group consisting of ether solvent, alcohol, lower alkane solvent and water.

5. A method for preparing the crystal form of ((5-nitroquinolin-8-yl)oxy)methyl-isobutyryl-L-prolinate according to claim 1, characterized in that, the method comprises the following steps of:

mixing Solution II containing ((5-nitroquinolin-8-yl)oxy)methyl-isobutyryl-L-prolinate and a solvent at a temperature ranging from room temperature to 50° C., and performing centrifugation to obtain the crystal form;

the solvent is one or more solvents selected from the group consisting of $C_1$-$C_6$ alcohol solvent, ester solvent, ether solvent, lower alkane solvent, lower halogenated alkane solvent, ketone solvent, aromatic hydrocarbon solvent, nitrile solvent, dimethyl sulfoxide and water.

TABLE 19

Stability of crystal form A

| | | | | Related substance 1 | | | | | | |
|---|---|---|---|---|---|---|---|---|---|---|
| Inspection conditions | Time | Appearance | Moisture | Impurity 1 | Impurity 2 | 5-Nitro-8-hydroxy-quinoline | Maximum unknown single impurity | Total impurities | Related substance 2 | Content |
| 40° C., | 0 | Yellow solid | 0.09% | 0.27% | N.D. | 0.04% | RRT 1.126: 0.07% | 0.53% | 0.06% | 101.1% |
| 75% RH | 1 M | Yellow solid | 0.06% | 0.27% | N.D. | 0.02% | RRT 1.125: 0.06% | 0.52% | 0.05% | 101.1% |
| | 2 M | Yellow solid | 0.09% | 0.27% | 0.01% | N.D. | RRT 1.132: 0.05% | 0.44% | 0.06% | 98.8% |
| | 3 M | Yellow solid | 0.06% | 0.32% | N.D. | N.D. | RRT 1.123: 0.05% | 0.49% | 0.10% | 99.3% |
| | 6 M | Yellow solid | <0.1% | 0.3% | <0.01% | <0.1% | RRT 0.896: 0.04% | 0.6% | 0.15% | 99.7% |
| 25° C., | 0 | Yellow solid | 0.09% | 0.27% | N.D. | N.D. | RRT 1.126: 0.07% | 0.53% | 0.06% | 101.1% |
| 60% RH | 3 M | Yellow solid | 0.07% | 0.32% | <0.01% | N.D. | RRT 1.123: 0.06% | 0.51% | 0.04% | 99.3% |
| | 6 M | Yellow solid | <0.1% | 0.3% | <0.01% | N.D. | RRT 1.121: 0.06% | 0.5% | 0.04% | 99.8% |
| 5 ± 3° C. | 0 | Yellow solid | 0.09% | 0.27% | N.D. | 0.04% | RRT 1.126: 0.07% | 0.53% | 0.06% | 101.1% |
| | 6 M | Yellow solid | 0.1% | 0.3% | <0.01% | N.D. | RRT 1.121: 0.07% | 0.5% | 0.03% | 99.6% |

6. The method according to claim 5, characterized in that, the solvent is a mixed solvent of $C_1$-$C_6$ alcohol and water, a mixed solvent of ether and lower alkane, a mixed solvent of ketone and lower alkane, a mixed solvent of ketone and ether, a mixed solvent of ester and $C_1$-$C_6$ alcohol, a mixed solvent of aromatic hydrocarbon and lower alkane, a mixed solvent of ketone and $C_1$-$C_6$ alcohol or a mixed solvent of ether and ester;

the volume ratio of the former to the latter in the mixed solvent is 1:8-1:1.

7. The method according to claim 5, characterized in that, the method further comprises the following steps of:

suspending a crystal form or amorphous form of ((5-nitroquinolin-8-yl)oxy)methyl-isobutyryl-L-prolinate in a solvent at a temperature of 50° C., and then performing stirring and centrifugation to obtain the crystal form;

the solvent is one or more solvents selected from the group consisting of $C_1$-$C_6$ alcohol solvent, ester solvent, ketone solvent, ether solvent, lower alkane solvent, aromatic hydrocarbon solvent, nitrile solvent and water.

8. A method for preparing the crystal form of ((5-nitroquinolin-8-yl)oxy)methyl-isobutyryl-L-prolinate according to claim 1, characterized in that, the method comprises the following steps of:

placing Solution III containing ((5-nitroquinolin-8-yl)oxy)methyl-isobutyryl-L-prolinate and a solvent in a cycle of 50° C.→5° C.→50° C. for one to five cycles, until solid precipitation, and performing solid-liquid separation to obtain the crystal form; or, heating the Solution III to 50° C. for dissolving, performing hot filtration, cooling the filtrate to 5° C. to −20° C., and performing solid-liquid separation to obtain the crystal form;

the solvent is one or more, solvents selected from the group consisting of $C_1$-$C_6$ alcohol solvent, ester solvent, ketone solvent, ether solvent, lower alkane solvent, aromatic hydrocarbon solvent and water.

9. The method according to claim 8, characterized in that, the solvent is a mixed solvent of $C_1$-$C_6$ alcohol and water, a mixed solvent of $C_1$-$C_6$ alcohol and ether, a mixed solvent of ketone and ester, a mixed solvent of aromatic hydrocarbon and ester or a mixed solvent of ketone and lower alkane;

the volume ratio of the former to the latter in the mixed solvent is 1:20 to 2:1.

10. A method for preparing the crystal form of ((5-nitroquinolin-8-yl)oxy)methyl-isobutyryl-L-prolinate according to claim 1, characterized in that, the method comprises the following steps of:

placing an open first container with a crystal form or amorphous form of ((5-nitroquinolin-8-yl)oxy)methyl-isobutyryl-L-prolinate solid in a second container with a solvent, sealing the second container, leaving it to stand at room temperature, and collecting the product when it is observed that the solid becomes wet or there is solid precipitation to obtain the crystal form;

the solvent is one or more solvents selected from the group consisting of $C_1$-$C_6$ alcohol solvent, ether solvent, ketone solvent, ester solvent, aromatic hydrocarbon solvent, dimethyl sulfoxide and water.

11. A method for preparing the crystal form of ((5-nitroquinolin-8-yl)oxy)methyl-isobutyryl-L-prolinate according to claim 1, characterized in that, the method comprises the following steps of:

placing an open first container with Solution IV containing ((5-nitroquinolin-8-yl)oxy)methyl-isobutyryl-L-prolinate and a positive solvent in a second container with an anti-solvent, sealing the second container, leaving it to stand at room temperature, and collecting the product when it is observed that the solid becomes wet or there is solid precipitation to obtain the crystal form;

the positive solvent is one or more solvents selected from the group consisting of $C_1$-$C_6$ alcohol solvent, ether solvent and ketone solvent; the anti-solvent is one or more of lower alkane solvent, ether solvent, alcohol solvent and water;

the volume ratio of the positive solvent to the anti-solvent is 1:20 to 2:1.

12. A method for preparing the crystal form of ((5-nitroquinolin-8-yl)oxy)methyl-isobutyryl-L-prolinate according to claim 1, characterized in that, the method comprises the following steps of:

volatilizing Solution V containing ((5-nitroquinolin-8-yl)oxy)methyl-isobutyryl-L-prolinate and a solvent at room temperature, and collecting the precipitated solid to obtain the crystal form-A;

the solvent is one or more solvents selected from the group consisting of $C_1$-$C_6$ alcohol solvent, ketone solvent, ester solvent, ether solvent, lower alkane solvent, aromatic hydrocarbon solvent, nitrile solvent, lower halogenated alkane solvent and water.

13. A crystal form of ((5-nitroquinolin-8-yl)oxy)methyl-isobutyryl-L-prolinate, characterized in that, the X-ray powder diffraction pattern thereof, which is obtained by using Cu-Kα irradiation and expressed in 2θ angle, comprises characteristic peaks at 5.44±0.2°, 10.90±0.2°, 14.09±0.2°, 16.17±0.2°, 17.92±0.2°, 20.66±0.2° and 23.13±0.2°.

14. The crystal form of ((5-nitroquinolin-8-yl)oxy)methyl-isobutyryl-L-prolinate according to claim 13, characterized in that, the X-ray powder diffraction pattern thereof, which is obtained by using Cu-Kα irradiation and expressed in 2θ angle, comprises characteristic peaks at 5.44±0.2°, 6.19±0.2°, 10.90±0.2°, 14.09±0.2°, 14.88±0.2°, 16.17±0.2°, 17.92±0.2°, 20.66±0.2°, 21.69±0.2° and 23.13±0.2°.

15. A method for preparing the crystal form of ((5-nitroquinolin-8-yl)oxy)methyl-isobutyryl-L-prolinate according to claim 13, characterized in that, the method comprises the following steps of:

mixing Solution A containing ((5-nitroquinolin-8-yl)oxy)methyl-isobutyryl-L-prolinate and a positive solvent with an anti-solvent to precipitate a solid, and performing solid-liquid separation to obtain the crystal form;

the positive solvent is one or more solvents selected from the group consisting of ester solvent;

the anti-solvent is an alkane solvent;

the volume ratio of the positive solvent to the anti-solvent is 1:20 to 2:1.

16. A pharmaceutical composition, characterized in that, it comprises the crystal form of ((5-nitroquinolin-8-yl)oxy)methyl-isobutyryl-L-prolinate according to claim 1 and an auxiliary material.

17. A method of treating an infectious disease or a cancer in a subject in need thereof, the method comprising administering to the subject a therapeutically effective amount of the pharmaceutical composition according to claim 16; wherein, the infectious disease is systemic infection, reproductive system infection or urinary system infection.

18. A pharmaceutical composition, characterized in that, it comprises the crystal form of ((5-nitroquinolin-8-yl)oxy)methyl-isobutyryl-L-prolinate according to claim 13 and an auxiliary material.

19. A method of treating an infectious disease or a cancer in a subject in need thereof, the method comprising administering to the subject a therapeutically effective amount of the pharmaceutical composition according to claim 18; wherein, the infectious disease is systemic infection, reproductive system infection or urinary system infection.

20. The method according to claim 4, characterized in that, the positive solvent is one or more solvents selected from the group consisting of ester solvent, $C_1$-$C_6$ alcohol solvent, ketone solvent, and ether solvent; wherein, the ester solvent is ethyl acetate; the $C_1$-$C_6$ alcohol solvent is one or more of methanol, ethanol, isopropanol and isobutanol; the ketone solvent is one or more of acetone, methyl ethyl ketone and methyl isobutyl ketone; the ether solvent is tetrahydrofuran and/or 1,4-dioxane;

the anti-solvent is one or more solvents selected from the group consisting of ether solvent, alcohol and lower alkane solvent; wherein, the ether solvent is one or more of methyl tert-butyl ether, diethyl ether and petroleum ether; the alcohol is a $C_1$-$C_6$ alcohol; the lower alkane solvent is one or more of n-heptane, n-hexane and n-octane.

21. The method according to claim 4, characterized in that, the positive solvent is an ester solvent; and the anti-solvent is an ether solvent.

22. The method according to claim 4, characterized in that, the volume ratio of the positive solvent to the anti-solvent is 1:20 to 2:1.

23. The crystal form of ((5-nitroquinolin-8-yl)oxy) methyl-isobutyryl-L-prolinate according to claim 14, characterized in that, the X-ray powder diffraction pattern thereof, which is obtained by using Cu-Kα irradiation and expressed in 2θ angle, comprises characteristic peaks at 5.44±0.2°, 6.19±0.2°, 8.06±0.2°, 10.90±0.2°, 12.18±0.2°, 14.09±0.2°, 14.88±0.2°, 16.17±0.2°, 17.92±0.2°, 20.66±0.2°, 21.69±0.2°, 23.13±0.2°, 24.42±0.2° and 26.03±0.2°.

24. The method according to claim 17, characterized in that, the cancer is bladder cancer or prostate cancer.

25. The method according to claim 19, characterized in that, the cancer is bladder cancer or prostate cancer.

* * * * *